US010076137B2

(12) United States Patent
Krietzman

(10) Patent No.: US 10,076,137 B2
(45) Date of Patent: Sep. 18, 2018

(54) VAPORIZER AND VAPORIZER CARTRIDGES

(71) Applicant: Mark Krietzman, Palos Verdes Estates, CA (US)

(72) Inventor: Mark Krietzman, Palos Verdes Estates, CA (US)

( * ) Notice: Subject to any disclaimer, the term of this patent is extended or adjusted under 35 U.S.C. 154(b) by 310 days.

(21) Appl. No.: 15/045,410

(22) Filed: Feb. 17, 2016

(65) Prior Publication Data

US 2016/0235122 A1 Aug. 18, 2016

Related U.S. Application Data

(60) Provisional application No. 62/270,557, filed on Dec. 21, 2015, provisional application No. 62/208,786, filed on Aug. 23, 2015, provisional application No. 62/184,396, filed on Jun. 25, 2015, provisional application No. 62/127,817, filed on Mar. 3, 2015, provisional application No. 62/116,926, filed on Feb. 17, 2015.

(51) Int. Cl.

| | |
|---|---|
| ***A61M 16/00*** | (2006.01) |
| ***A24F 47/00*** | (2006.01) |
| ***H05B 1/02*** | (2006.01) |
| ***A24B 15/16*** | (2006.01) |
| ***H05B 3/14*** | (2006.01) |
| ***H05B 3/42*** | (2006.01) |

(52) U.S. Cl.

CPC ............ *A24F 47/008* (2013.01); *A24B 15/16* (2013.01); *H05B 1/0225* (2013.01); *H05B 1/0244* (2013.01); *H05B 3/146* (2013.01); *H05B 3/42* (2013.01); *H05B 2203/014* (2013.01); *H05B 2203/021* (2013.01); *H05B 2203/022* (2013.01)

(58) Field of Classification Search

None

See application file for complete search history.

(56) References Cited

U.S. PATENT DOCUMENTS

| | | | | |
|---|---|---|---|---|
| 5,269,327 A * | 12/1993 | Counts | .................. | A24F 47/008 128/200.14 |
| 5,388,594 A * | 2/1995 | Counts | .................. | A24F 47/008 128/202.21 |
| 5,530,225 A * | 6/1996 | Hajaligol | ............. | A24F 47/008 131/194 |
| 5,649,554 A * | 7/1997 | Sprinkel | ............... | A24F 47/008 128/202.21 |

(Continued)

FOREIGN PATENT DOCUMENTS

| | | |
|---|---|---|
| CN | 204393344 * | 6/2015 |

*Primary Examiner* — Thor Campbell

(57) ABSTRACT

Disclosed herein are methods and systems to vaporize extract, plant material containing organic material and the like, including utilizing a cartridge which may be disposable. The cartridge may be heated in zones or portions. The cartridge may form the inhalation pathway thereby reducing the accumulation of dirt and odor in the heating device. One disclosed vaporizer system has a base with a cartridge interface, a heater element, an on/off switch, a battery, a temperature sensor in proximity to the heater element; a controller in signal communication with the heater element, battery, temperature sensor and the on/off switch; that mates with a disposable cartridge.

4 Claims, 17 Drawing Sheets

(56) References Cited

U.S. PATENT DOCUMENTS

| | | | | | |
|---|---|---|---|---|---|
| 5,692,525 | A * | 12/1997 | Counts | A24F 47/008 | 131/194 |
| 5,708,258 | A * | 1/1998 | Counts | A24F 47/008 | 131/194 |
| 5,954,979 | A * | 9/1999 | Counts | A24F 47/008 | 131/194 |
| 9,032,968 | B2 * | 5/2015 | Glasberg | A24F 47/008 | 131/273 |
| 9,271,526 | B2 * | 3/2016 | Liu | A24F 15/12 | |
| 9,675,117 | B2 * | 6/2017 | Li | A61M 15/06 | |
| 9,775,380 | B2 * | 10/2017 | Fernando | A24F 47/008 | |
| 9,826,780 | B2 * | 11/2017 | Krietzman | A24F 47/008 | |
| 2004/0089314 | A1 * | 5/2004 | Felter | A24F 47/008 | 131/194 |
| 2007/0074734 | A1 * | 4/2007 | Braunshteyn | A24F 13/00 | 131/328 |
| 2014/0014124 | A1 * | 1/2014 | Glasberg | A24F 47/008 | 131/328 |
| 2014/0202476 | A1 * | 7/2014 | Egoyants | A24F 47/008 | 131/329 |
| 2014/0366898 | A1 * | 12/2014 | Monsees | A24F 47/008 | 131/329 |
| 2015/0040929 | A1 * | 2/2015 | Hon | A24F 47/008 | 131/329 |
| 2015/0150308 | A1 * | 6/2015 | Monsees | A24F 47/006 | 131/329 |
| 2015/0305406 | A1 * | 10/2015 | Li | A24F 47/008 | 131/329 |
| 2015/0342257 | A1 * | 12/2015 | Chen | H05B 3/06 | 392/390 |
| 2016/0198771 | A1 * | 7/2016 | Goggin | A24F 47/008 | 131/329 |
| 2016/0255879 | A1 * | 9/2016 | Paprocki | A24F 47/008 | |
| 2017/0156407 | A1 * | 6/2017 | Abramov | A24F 47/008 | |

* cited by examiner filter or flavor 12
Heater 20
Heating element 40
receiver 23
T sensor 34
case 22
battery 25
zone A
zone B
zone C
zone N
on/off
27
Controller
30
Zone AA
Zone BB
Zone CC
Zone NN 401
402
403
406
407
408
410A
410B
412
207
404
"F"
"S"
416
417
"A"
"B"
400
500
"AIE"
"IE"
420

VAPORIZER AND VAPORIZER CARTRIDGES

RELATED APPLICATION

This application claims the priority to United States ("U.S.") Provisional Patent Application Ser. No. 62/116,926 entitled CARTRIDGE AND HEATER filed on 17 Feb. 2015, the disclosure of which is incorporated by reference herein in its entirety.

Additionally, this application also claims the priority to U.S. Provisional Patent Application Ser. No. 62/127,817 entitled MULTI ZONE VAPORIZER filed on 3 Mar. 2015, the disclosure of which is incorporated by reference herein in its entirety.

Furthermore, this application also claims the priority to U.S. Provisional Patent Application Ser. No. 62/184,396 entitled VAPORIZER DEVICE AND METHOD 25 Jun. 2015, the disclosure of which is incorporated by reference herein in its entirety.

Furthermore, this application also claims the priority to U.S. Provisional Patent Application Ser. No. 62/208,786 entitled VAPORIZER CARTRIDGE AND HEATER 23 Aug. 2015, the disclosure of which is incorporated by reference herein in its entirety.

Still furthermore, this application also claim priority to U.S. Provisional Patent Application Ser. No. 62/270,557 entitled THIN CONVECTION VAPORIZER filed 21 Dec. 2015 the disclosures of which is incorporated by reference herein in their entirety as if fully set forth herein.

BACKGROUND OF THE DISCLOSURE

Field of the Disclosure

The present disclosure relates generally to heating system and device that releases organic residues from essential oils, extracts and plant based material upon appropriate heating and releases or vaporizes the organics without combustion.

Related Art

Vaporizer for plant based materials and essential oils and exist. Vaporizers which allow a fluid gas containing the vapor and other residues to follow a fluid pathway from source of vapor to user inhalation exist. *Cannabis* and other botanicals have been known in the art to be vaporized or burned to release organic material in the form of inhalable material. Vaporizing at correct temperatures can boil off the oils for inhalation without combusting the plant material.

*Cannabis sativa* contains over 421 different chemical compounds, including over 60 cannabinoids. Cannabinoid plant chemistry is far more complex than that of pure Tetrahydrocannabinol (THC), and different effects may be expected due to the presence of additional cannabinoids and other chemicals. Eighteen different classes of chemicals, including nitrogenous compounds, amino acids, hydrocarbons, carbohydrates, terpenes, and simple and fatty acids, contribute to the known pharmacological properties of *cannabis.*

*Cannabis*, for example has a narrow range at which it can be heated to release "THC", or more precisely its main isomer (−)-trans-$\Delta^9$-tetrahydrocannabinol) and CBDs (Cannabidiol loosely referring to as many as 85 identified compounds in *Cannabis*) chemicals as vapor without burning the organic material and adding non-THC and CBD material to the inhalation gases.

Heating a chamber loaded with organic material may, in some instances, overheat at least portions thereof and therefore combust, overheat or otherwise release unwanted items which may include carcinogens and chemicals into the vapor.

*Cannabis* oil containing vapor condenses as it cools. When moving through a flow path such vapor, as they condense, coat surface of a vaporizer with sticky residue which is both pungent and hard to remove. Removal requires chemicals and odors are very long lasting.

It is therefore a desideratum to have a device, method and or system wherein such heating is better managed and/or residues and odors are minimized.

DESCRIPTION

A method, system and device is disclosed which can at least one of reduce and eliminate the clogging of a fluid pathway in a vaporizer for inhalation of organic material via a output connected directly to the fluid pathway.

A method, system and device is disclosed which can at least one of reduce the odor in and about a heating chamber in a vaporizer.

Aspects of vaporizer systems and methods disclosed include a base having a cartridge interface to receive a disposable cartridge comprising; a heater element; an on/off switch; a battery; an illuminated indicator; a temperature sensor in proximity to the heater element; a controller in signal communication with the heater element, battery, indicator, temperature sensor and the on/off switch; a disposable cartridge; and, whereby pressing the on/off switch turns on power to the heater.

Aspects of vaporizer systems and methods disclosed include a base having a cartridge interface to receive a disposable cartridge comprising; a heater element; an on/off switch; a battery; an illuminated indicator; a temperature sensor in proximity to the heater element; a controller in signal communication with the heater element, battery, indicator, temperature sensor and the on/off switch; a disposable cartridge with a section for containment of material to vaporize in the cartridge forming an air intake end "AIE"; a section forming an inhalation end "IE"; and, the second section is inserted into the cartridge interface and positioned in thermal contact with the heater element whereby heat of at least 400 degrees F. can transfer from the heater element through the cartridge into the material; and, whereby pressing the on/off switch turns on power to the heater. In some instances an alignment key and guide system may be added to orient the cartridge. In some instances visual cues may be added on the cartridge which correspond to the placement of cartridge portions of the containment second section over the heater element. In some instance positional tabs formed on the cartridge will communicate with an actuator in the case adjacent to the cartridge interface; and, the actuator communicates the movement of a positional tab to the controller during the heating and vaporizing process.

Aspects of vaporizer systems and methods disclosed include a controller stops heating when a fixed time is met and/or applies heat at a selected exposure temperatures (SET) to a portion of the containment area in a cartridge accordance with fixed times. In some instances the controller prohibits heating until a cartridge is moved linearly in the interface. In some instances the controller prohibits heating until a cartridge is in the interface.

Aspects of vaporizer systems and methods disclosed include a vaporizer system with a disposable cartridge having a case with a cartridge interface to receive a disposable cartridge comprising; a heater manifold with an inlet and an outlet; a heating element within the manifold; an on/off switch; a battery; a temperature sensor in proximity to the outlet; a controller in signal communication with the heater element, battery, temperature sensor and the on/off switch; a disposable cartridge; and, whereby pressing the on/off switch turns on power to the heater. In some instances a signal communication light in signal communication with the controller which one of changes color, lights up, flashes and goes steady state when the temperature in the manifold is at SET to instruct the user to inhale. In some instances the controller keeps the heat in the manifold generally at the SET for a fixed time.

Aspects of vaporizer systems and methods disclosed include a vaporizer system with a disposable cartridge which has distal end containing material and a proximal end separated by a divider which fits into a case with a cartridge interface to receive a disposable cartridge comprising; a heater manifold with an inlet and an outlet; a heating element within the manifold; an on/off switch; a battery; a temperature sensor in proximity to the outlet; a controller in signal communication with the heater element, battery, temperature sensor and the on/off switch; a disposable cartridge; and, whereby pressing the on/off switch turns on power to the heater.

Aspects of vaporizer systems and methods disclosed include a vaporizer system having a case with a heating chamber to receive a disposable cartridge with an open top which mates with a cover; a heater manifold with an inlet vent and an outlet vent; a first cutting element in the bottom of the heating chamber with the outlet vent passing there through; a heating element within the manifold; an on/off switch; a battery; a temperature sensor in proximity to the outlet; a controller in signal communication with the heater element, battery, temperature sensor and the on/off switch; a cover having an intake with a fluid pathway therethrough which mates with the open top; a disposable cup cartridge;

whereby pressing the cup cartridge into the heating chamber causes the first cutting element to pierce the bottom of the cup cartridge; and, whereby pressing the on/off switch turns on power to the heater. In some instances the manifold further comprises:

air intake vents into the manifold; and, heated air vents for air exiting the manifold to enter the cartridge. In some instances the cup cartridge has a frangible cover and a second cutting element associated with the fluid pathway is added whereby the second cutting element pierces the frangible top when cover is mated to the case forming a fluid pathway for vapor.

FIGURES

The invention may be better understood by referring to the following figures. The components in the figures are not necessarily to scale, emphasis instead being placed upon illustrating the principles of the invention. In the figures, like reference numerals designate corresponding parts throughout the different views.

Figures 16, 17, 18, 19A, 19B, 20:
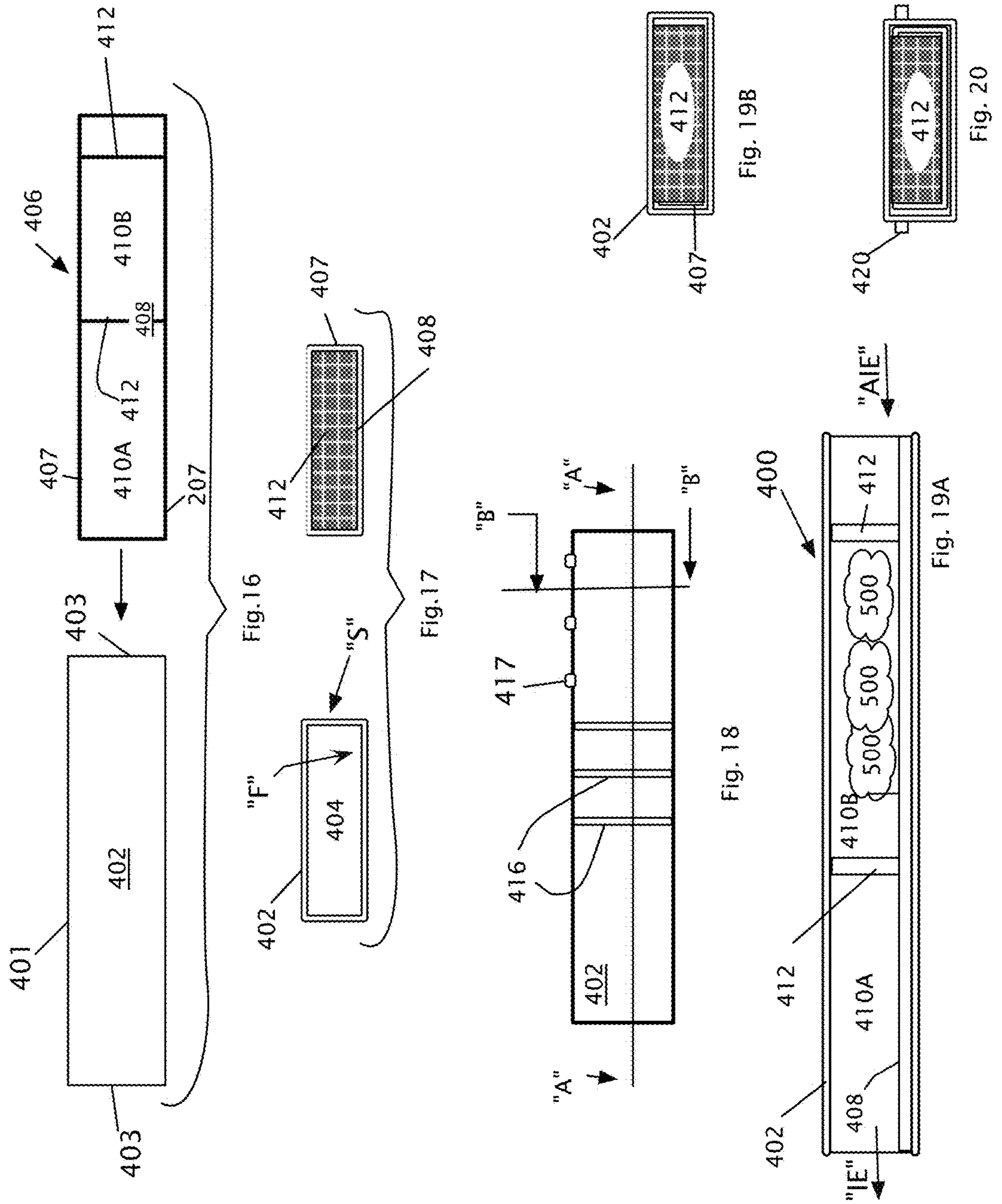
FIGS. 16 and 17 illustrate aspects of disposable cartridges for use with cartridge interface heater.
FIG. 18 illustrates an assembled cartridge.

FIGS. 19A and 19B illustrated cut-away views of the cartridge of FIG. 18 along the lines of A-A and B-B.

FIG. 20 illustrates a cartridge with alignment key to limit up-down insertion to one orientation.

Figures 21A, 21B, 21C, 22A, 22B:
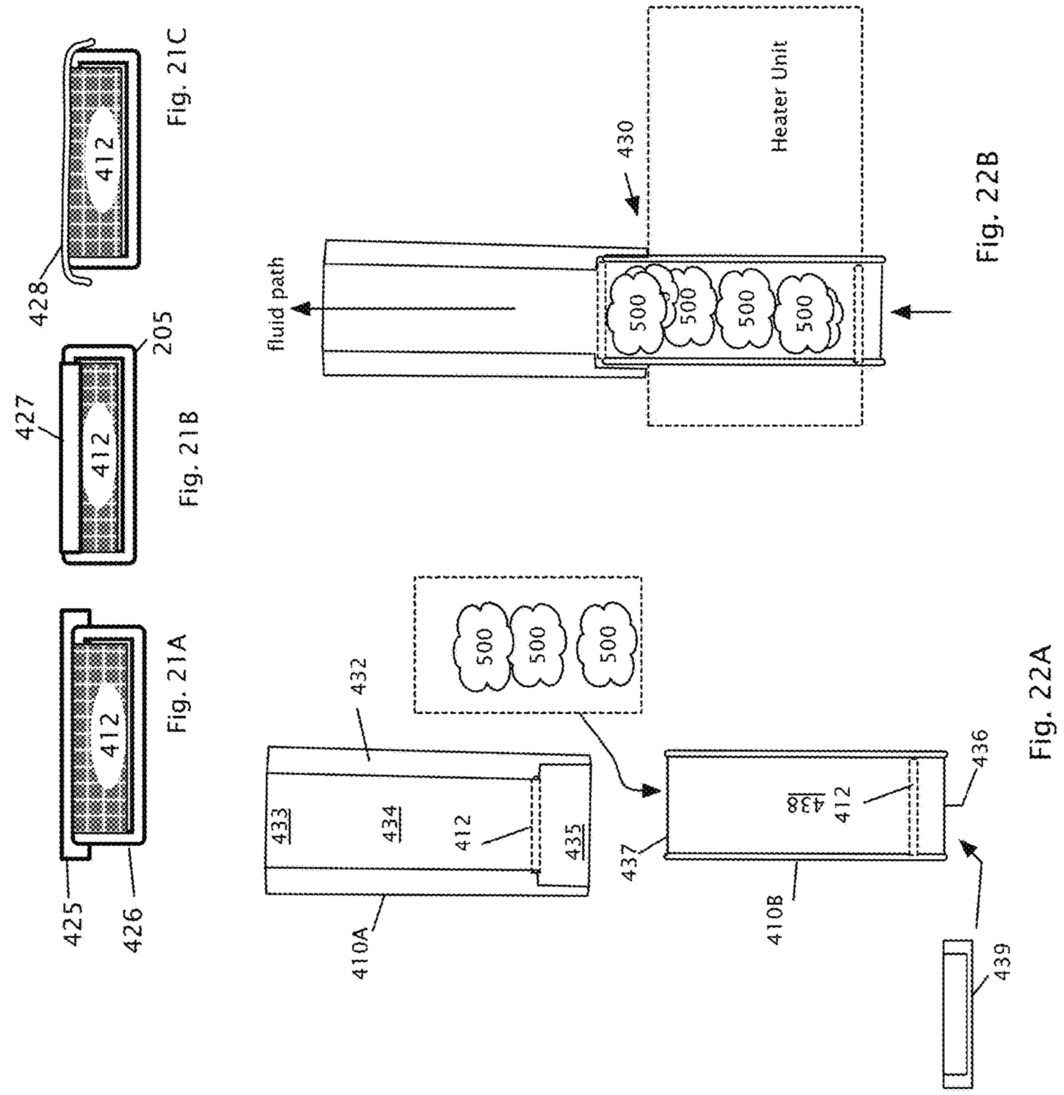

FIGS. 21A-21C illustrate alternative covers for disposable cartridges.

FIGS. 22A-22B illustrate a tubular fillable cartridge.

Figure 23D:
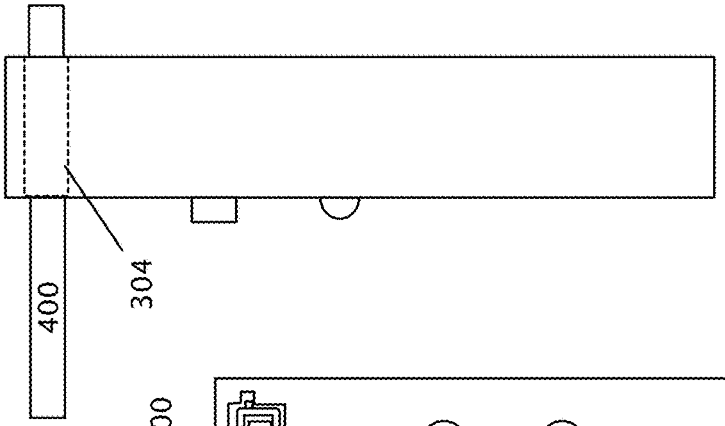
Figure 23C:
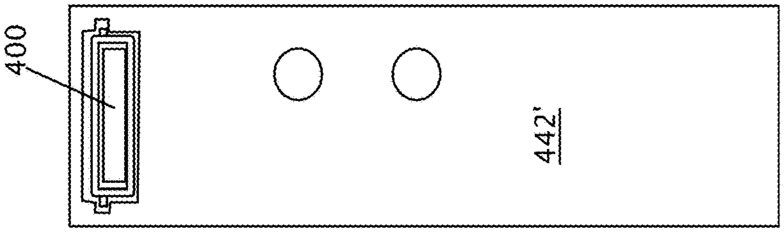
Figure 23B:
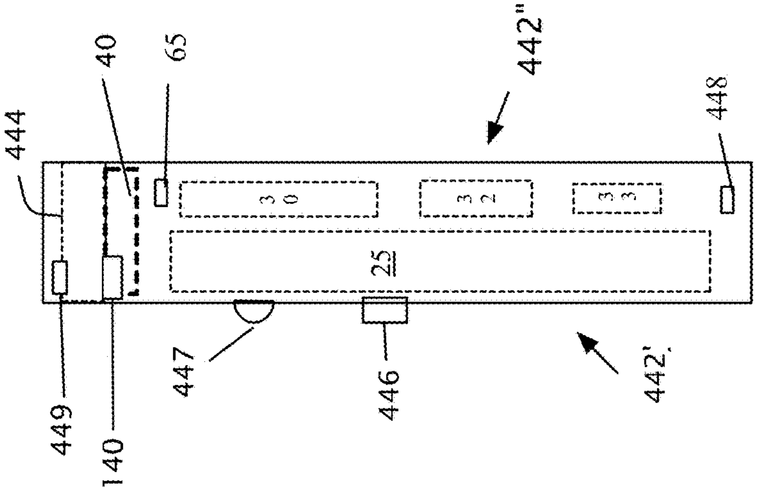
Figure 23A:
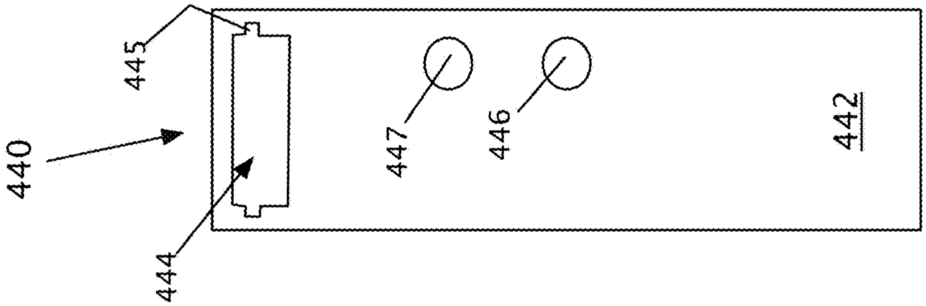

FIGS. 23A-22G illustrate a heater with disposable cartridge interface and use of the heater with a movable cartridge.

Figure 24:
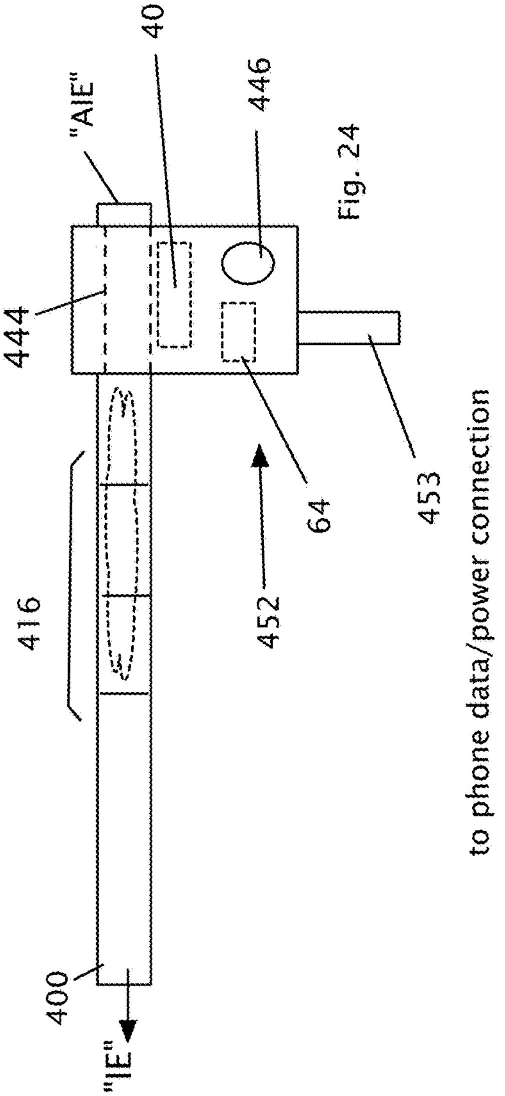
Figure 25:
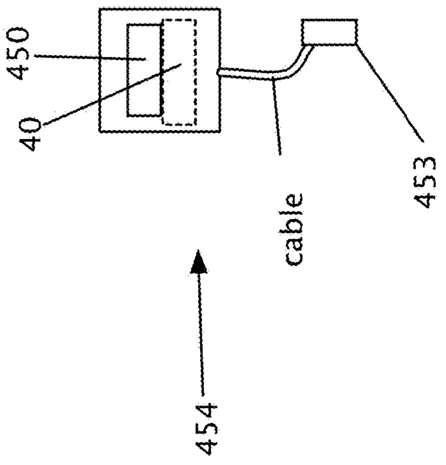

FIGS. 24 and 25 illustrate heater devices for use with a smartphone or other power supply.

Figure 26:
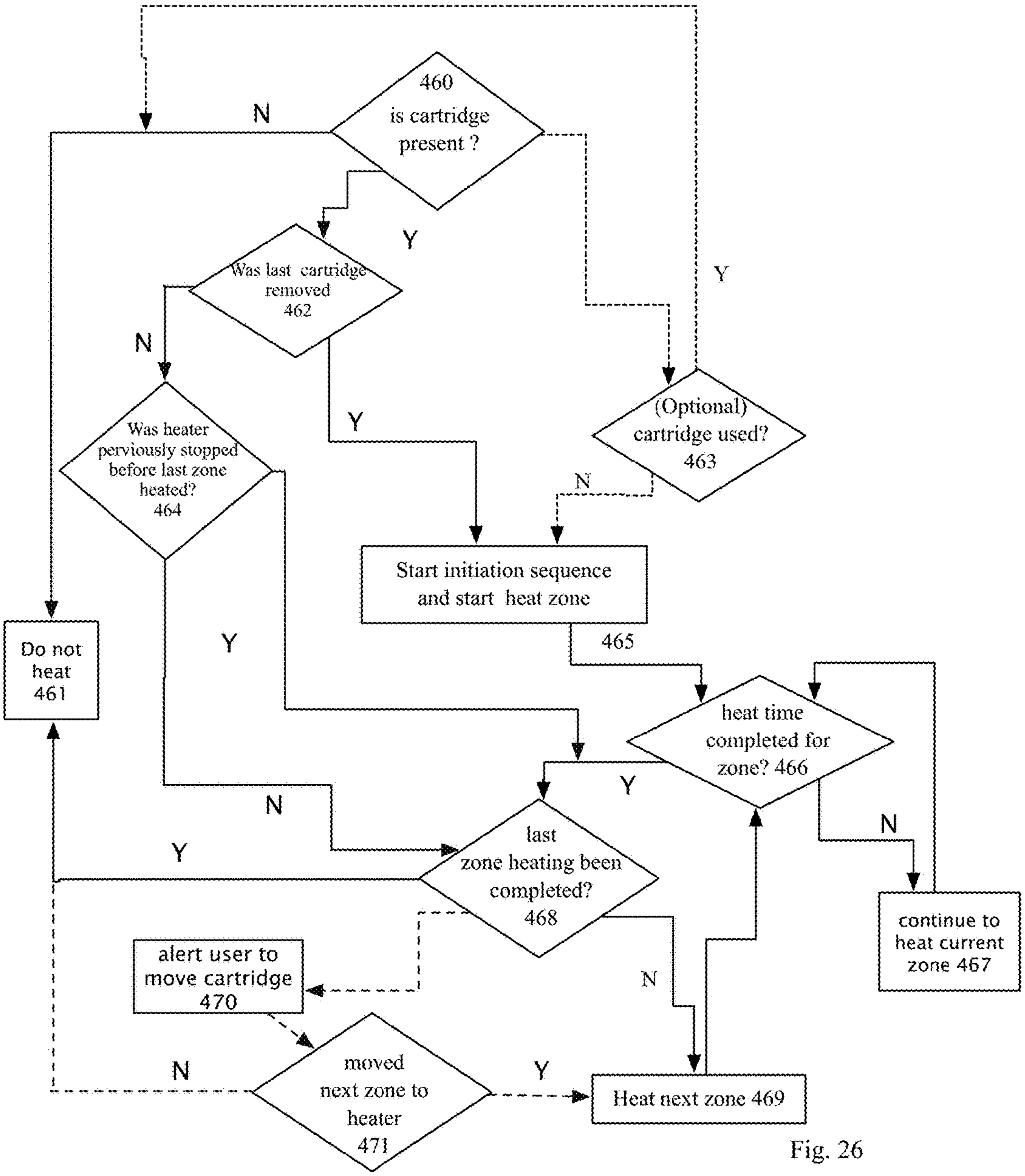

FIG. 26 shows aspects of controller logic for heating zones in a multi-zone vaporizer device.

All descriptions and callouts in the Figures and all content therein are hereby incorporated by this reference as if fully set forth herein.

Further Description

A vaporizer system, device and method which provides for heating of a cartridge or a section thereof is disclosed. Cartridges are preferably disposable but in some instances may be refillable. Vaporizing plant material for inhalation of plant borne chemicals is considered by some to be less harmful then combusting the plant material. Tobacco and *cannabis* are examples of such material.

Traditional portable vaporizers provide a flow pathway from heating unit to inhalation path to user. Those pathways and the heating chamber become covered with sticky residue of organic materials, oils and plant material. When vaporizing extracts or oils a carrier or binder material or substrate may be in the heating chamber of traditional devices forming waste products and odors. These wastes and residues must be removed and can be are hard to remove, the can block fluid passage and they are odiferous.

The instant disclosure teaches refillable cartridges and disposable inhalation cartridges for use with and in a heater base wherein the cartridge contains the organic material to be vaporized. Cartridges may be tubular, conical, or flat. Some cartridges are multipart. Cartridges may have sections which are formed of different materials with different properties to facility at least one of strength, insulation, conduction, ease of use, thermal transfer for heating, and containment for the plant material or for extract therein. In some instance a cartridge is disposable having contained material for vaporization to prevent direct contact with the heater or a heater chamber thereby reducing the clogging, odiferousness, vapor condensate material or other build up within the heater or heating chamber. In some instance the fluid pathway from the organic material to the inhalation point is integral to the cartridge and disposable thereby reducing the clogging, odiferousness, vapor condensate material or other build up in the fluid pathway.

In some instances the heater is a single heater placed or moved into proximity with the material (in the cartridge) to vaporize wherein heat is supplied to and through the cartridge or a portion thereof. In some instances a controller, such as a microprocessor with hardware and/or software logic turns on/off heating element. In some instance multiple heating elements are used to form zones to heat different sections of the cartridge at different times.

In some instances the cartridge has limited orientations of insertion to hold it fixed in the heater and unable to rotate about its axis. In some instances the cartridge has a frangible tab or identifier which is broken on insertion to prevent reuse of a spent cartridge. In some instances the cartridge is marked with an identifier that is stored in memory to turn off the heater if the cartridge has already been used.

The instant disclosure also teaches aspects of one or more reusable inhalation cartridges (also sometimes referred to as carriages) and a heater base wherein the cartridge has a chamber containing organic material to be vaporized. A fluid pathway for air to pass through organic material being heated for vaporization to the inhalation point is integral to the cartridge. In some instances heater elements are arrayed and the controller or controllers turn heater elements on/off to apply heat to a selected portion or portions of the cartridge at a time. In other instances the cartridge is moved across a single heater to bring a portion of the cartridge into close proximity to the heating element. In some instances tactile or visual cues are provided to a user to enable movement of the cartridge along a path between portions of the chamber for sequence local heating FIGS. 1, 2, 3, 4 and 5 show elongated cartridges 1 with two ends; the first end 2 is an inhalation (or intake) end or portion and the second end 3 is a containment (or heating) end or portion. During use a cartridge is mated with a case providing a heater, which is controlled to supply heat, or heated air at a predetermined temperature to cause vaporization. For vaporization and ingestion of vapor, air is drawn into the cartridge by inhalation (not shown) into the open front 5 to the containment end 3 and then through the inhalation end 2, vapor released from material in the cartridge will flow with the air moving through the cartridge, and finally air and vapor move out through the open back 6. An optional tab 7 (which may be a frangible section that is deformed during insertion) is provided. If frangible the tab's destruction may render the cartridge unusable because an actuator will not be bale to read the tab. In some instance an optional ID 8 is added which verifies cartridges status as used or not used via memory accessible from the controller. In some instances perforations 10 may be formed in the containment end 3 to reduce thermal resistance to heat flow from heating elements by the cartridge material. In some instances a filter or flavor filter 12 is placed in the inhalation end 2 whereby vapor inhaled passes. The filter can remove some materials from the vapor and the flavor filter adds an inhalable flavor to the vapor. A flow through divider 15 such as a screen or coarse filter which allows vapors to pass through may be positioned in the cartridge between the containment and inhalation ends. A flow through divider may also be positioned at or near the open end 5. Organic matter 500 is placed in the containment 3 for use of the cartridge. The organic material is a material containing oils or resins (such as *cannabis*), which can be released via heating. Extract containing organic material such as oils and resins extracted from *cannabis* may be paced in the cartridge. It may also be placed or bound with a binder or carrier material/compound. Carrier materials include but are not limited paper, wools, fabric, plastic, hemp, and other material that does not outgas toxic or harmful chemicals or fumes at the temperatures necessary to vaporize the extract.

The cartridge may be formed of a disposable material that will not burn or release toxic or harmful fumes at temperatures that are reached by the heater in the device. In generally for many organic materials the temperature of vaporization will be between 320 F to 420 F. The cartridge may be scarred by the heating process, as it is disposable. Paper, fibers such as cotton and hemp, metal, foil, plastic, resins, thermo plastics, wool, ceramics, ceramic-doped paper, glass, Polyether ether ketone (PEEK), and combination thereof may be suitable material for some or all of the cartridge. The cartridge maybe made of different materials for different regions. For example the containment portion 3 is subjected to the greatest heat. The material must be suitable to transfer a sufficient portion of the heat applied to its surface through its wall and into the containment portion to thereby cause vapor of the organic material 500.

The cartridge heating portion being constructed to withstand between about 3-12 minutes of periodic heating to a temperature adequate to vaporize oils or resins within *cannabis* without substantially burning the containment portion, intake (inhalation end) portion or the organic material.

During use the cartridge 1 is inserted in a heater 20 via the pathway of arrow 1000. This also may be referred to as a pass through cartridge device. The heater 20 has a case 22 with a receiver 23 (forming a guide or interface within the heater for the cartridge). The receiver interface 23 opens into a cartridge guide 24. The guide is a channel within the case that is open to allow passage of the cartridge therein. The guide refers to a region within the case that is roughly the perimeter of the cartridge. For conductive heating—proximity of the heating element o the cartridge may be preferable. Placing heating elements in the area of the cartridge guide positions the heater(s) adjacent to at least a portion of the cartridge. The cartridge and heater work as a system to heat the material in the cartridge.

Those of ordinary skill in the art will recognize that a less than complete [perimeter wrap of the cartridge is within the scope of this disclosure. A cartridge may be fitted in a three-sided receiver and partially extend out of it and still be within the scope of this disclosure.

Within the case is a battery 25. A cartridge identification reader 26 such as an optical reader, an emitter receiver, a pressure sensor and the like may also be added to the device. The identification reader is a sensor that verifies a cartridge ID and via vie the controller which may include utilizing the memory associated therewith. The controller determines if the cartridge has previously been used. The controller may determine that a heat indicator (such as a color change region) has previously been heated; it may determine that a code is ablated (by the heat of prior use) or is not present thereby preventing heating. An on/off switch 27 is shown, and battery may have a charging input/output (I/O) 28 (or it may be a replaceable battery). The case may also have a mechanical or electrical mechanical actuator 29 that is activated by the presence of the tab 7. Actuation is the communication of the actuator 29 to the controller whereby the controller 30 recognizes the cartridge as "inserted" (and in the case of a frangible tab it also conveys that the cartridge is new) and thereby allows the controller 30 to switch on electrical current to the heating element(s). Within the case is the controller 30. The controller is a microprocessor which may have memory 32 and which controls certain operations of the vaporizer device. Operations may include one or more of time, date, location, security code, on/off, sequence of heating, temperature, indicator display of the heater, battery charging, battery management, battery state of charge indication, cartridge verification. Those of ordinary skill in the art will recognize that BLUETOOTH®, WI-FI® 33 or other wireless or wired connection to a smart phone or computer may also be used to perform some of the controller functions and that would be within the scope of this disclosure. One or more temperature sensors 34 such as thermistors and thermocouples are within the case and near the receiver 23.

The case 22 contains one or more heating elements 40. One or more heater vents 42 may be provided. Although four heating elements are shown those of ordinary skill in the art will understand that what is disclosed is one or more zones. In some instance only a single heating zone may be provided, in other instances multiple zones may be utilized and such is within the scope of this disclosure.

In some exemplary implementations a multi-zone heater is disclosed it may have heat zone "A" to zone "N". A cartridge, during use, will have corresponding zones "AA" to "NN" which align generally with the heat zones.

During use one or more zones may be turned on to supply heat, via heating elements, to heat organic material 500 and release vapor. The vapor is drawn in via inhalation by the user. Sequencing the zones for heating is advantageous in that it can reduce peak power consumption. Sequencing the zones for heating is also advantageous in that it can release vapor from a discreet amount of organic material at one time thereby leaving unheated areas of organic material with the same cartridge for a next use. Many terpenes in vaporize at temperatures below the vaporization of THC and by sequence zone heating these terpenes are released in a sequence whereby a later inhalation or a second user inhalation which follows the first heating and inhalation will also receive terpenes. By zoned heating more of the plethora of cannabinoid present in the organic material are available form each discreetly heated zone then would be for material heated together.

Figures 1, 2, 3, 4, 5:
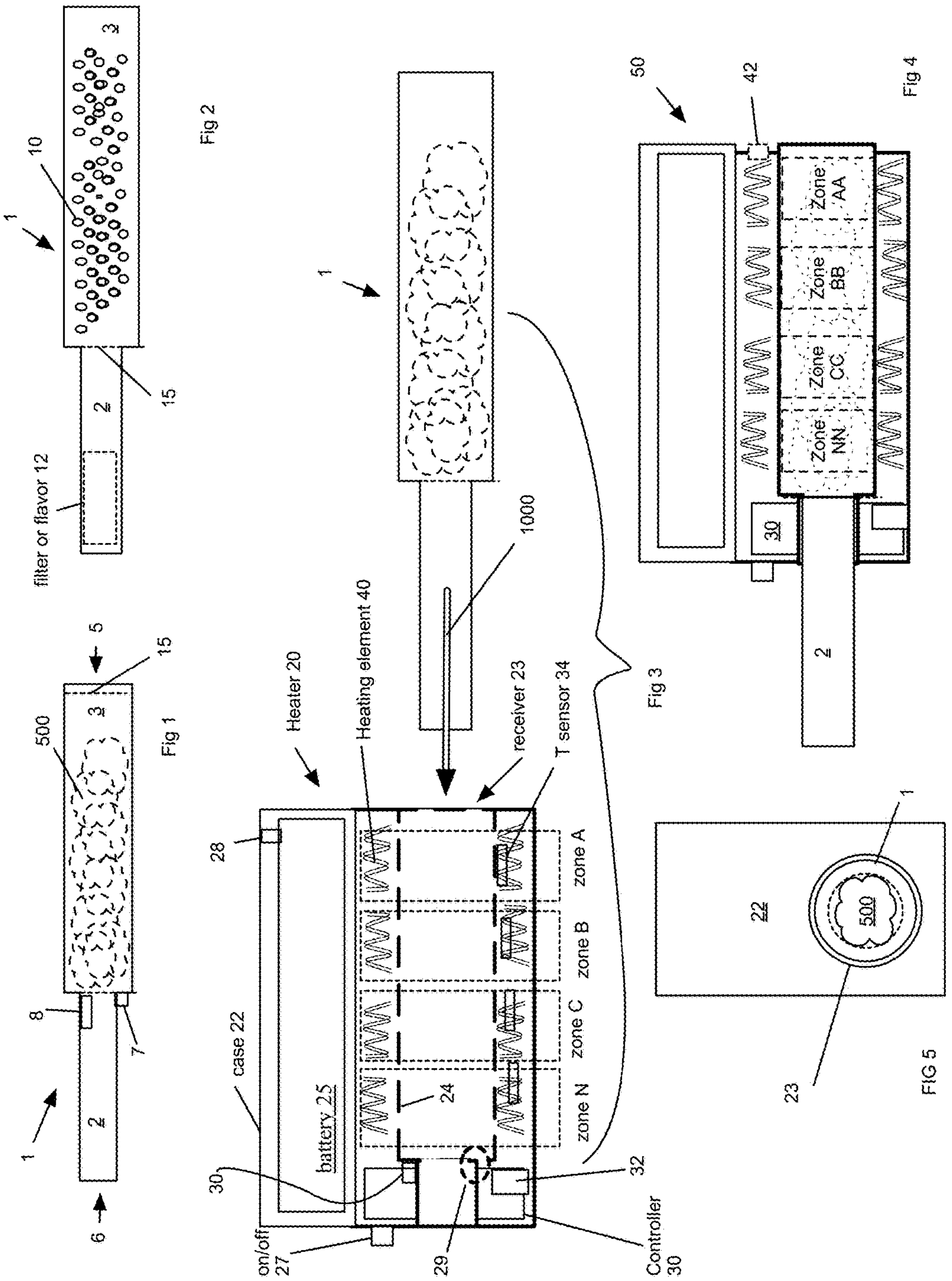
FIGS. 1-5 illustrate aspects of cartridge modules and associated heater.
Figure 6:
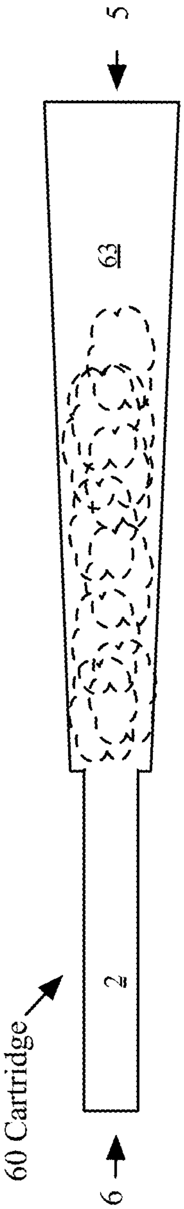
FIGS. 6-7 illustrate aspects of a cone cartridge module and associated heater.
Figure 7:
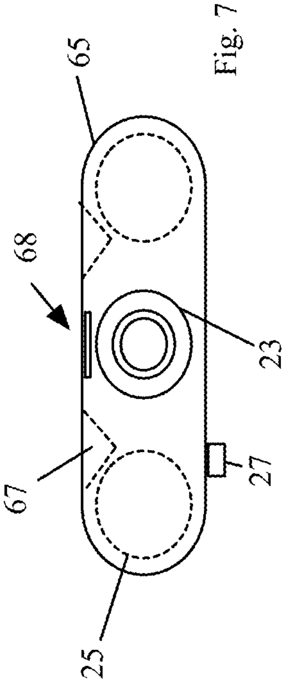

FIGS. 6 and 7 show aspects of another exemplary implementation of a cartridge containing organic material and a heater device. The cartridge 60 has a conical containment 63 and the receiver interface 23 is shaped to accommodate the conical shape.

Figure 8A:
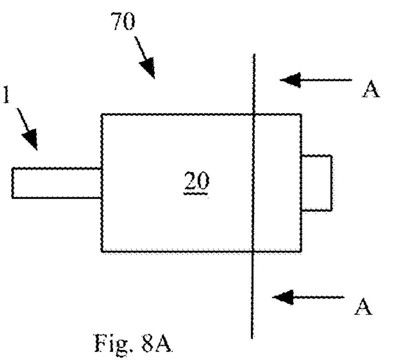
FIGS. 8A-8D illustrate aspects of a cartridge module and vertical heaters.
Figure 8B:
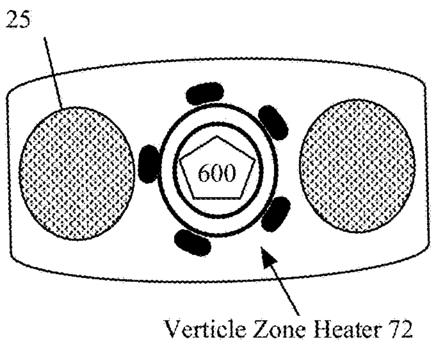
Figure 8C:
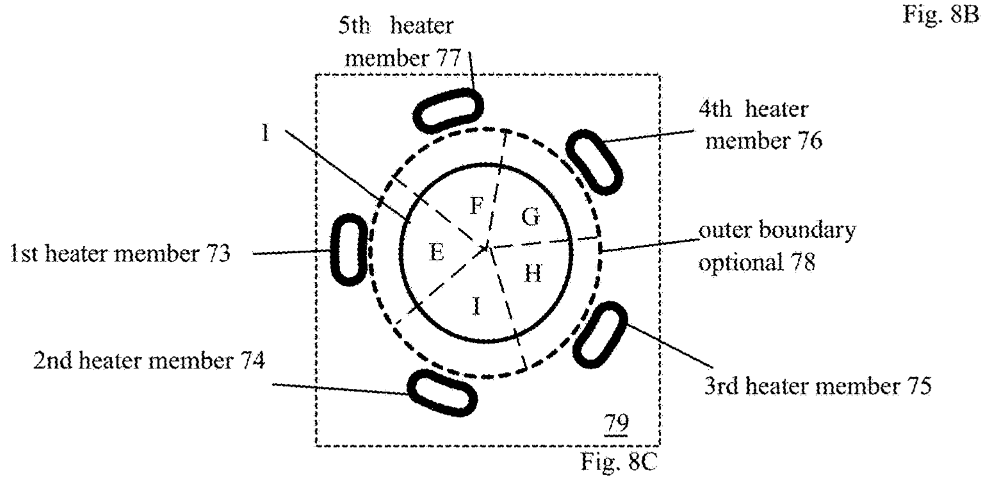
Figure 8D:
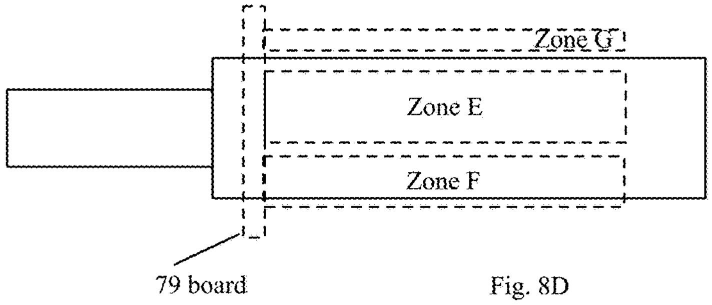

FIGS. 8A-8D shows aspects of another exemplary implementation of the cartridge and heater device. A heater 70 receives a disposable cartridge 1. FIG. 8B shows a view of the line "A-A" of FIG. 8A exposing vertical heating zone 72 and a key guide portion 600 to the receiver. The key limits cartridge entry to one configuration and prevents rotation about its axis. FIG. 8C is a view of the aspects of the vertical zone heater 72 showing the elements which are aligned with the cartridge 1 and how each element 73-77 forms a corresponding vertical heat zone E-I. An optional boundary 78 may be formed between the heater elements 73-77 and the cartridge 1. Accordingly, vertical heat zone "E" is heated by vertical zone heater element 73 and so on. A printed circuit board (PCB) or other support 79 may be used to support the heater elements 73-77 FIG. 8D shows a side view of a cartridge 1 with a representation of the location of vertical heat zones E-G.

Figure 9A:
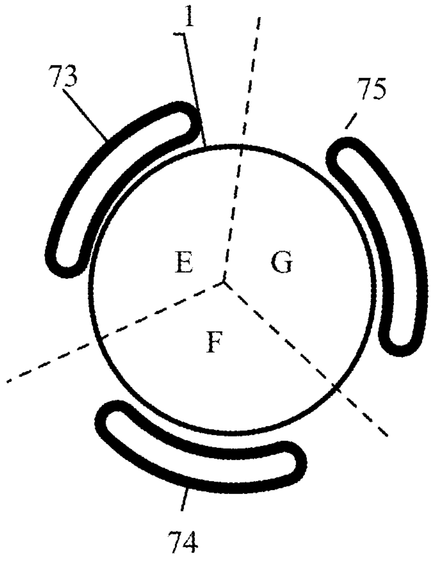
FIGS. 9A and 9B illustrate a front end view of a tubular cartridge with shaped zone heaters and a graph of heat distribution via the shaped heaters.
Figure 9B:
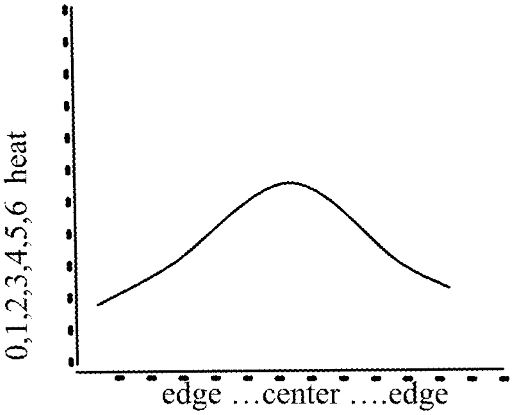

FIGS. 9A and 9B is an exemplary of a three elements 73-75 forming three vertical heat zones E-G, around a cartridge 1. The edge heat is less than the center heat, the heat is distributed in this optional configuration. Means to accomplish this include selection of heating element materials to generate more heat in the center, arraying a group of heating filaments to have a denser region of filaments to provide more heat near the center, using dissimilar heating filaments with the ones corresponding to the center being less conductive and providing less heat per/unit area, insulation over a portion of the heating element, and shaping the heating element to focus the radiation (heat) towards a center point corresponding roughly to the pie shaped regions (E-G).

Figure 10:
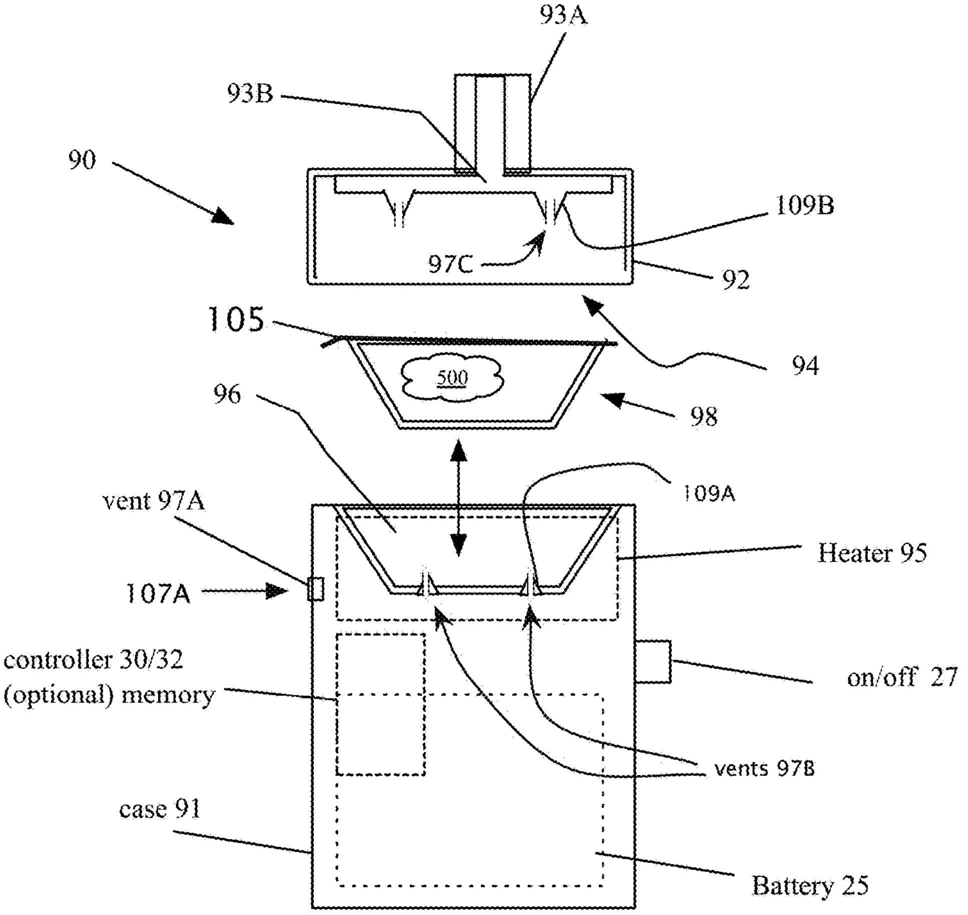
FIGS. 10-12 illustrate aspects of a disposable drop-in cartridge module and heater.
Figure 11:
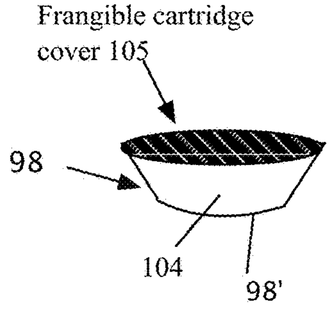
Figure 12:
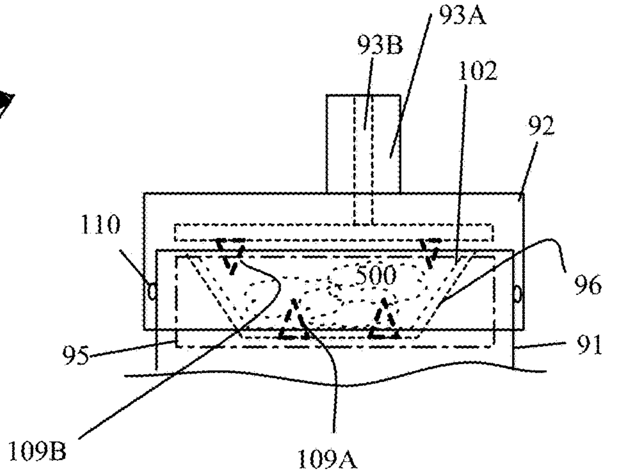

FIGS. 10-13 show cup cartridges in a heater systems. one disposable cup cartridge heating and vaporizing system 90 is shown in FIGS. 10-12. A case 91 and a cover 92 form the heating device. Not shown are the memory, battery and electrical connections. Through the cover and is an intake 93A and through the intake is a fluid pathway 93B which communicates to the inside of the device. The cover fits onto the case forming a closed unit with the fluid pathway in and out of the device. The cover 92 has an open bottom 94 to mate with the case 91. Within the case is a heater 95 a heater chamber 96 of a predefined shape and a vent 97A opening through which is a fluid pathway 107A from the exterior of the case 91 to the interior. Vents 97B are provide a fluid pathway through bottom of the chamber to the bottom 98' of the cup cartridge from cutting elements 109A into the cartridge and communicate from the interior of the case into the cartridge. The cover can have top cutting elements 109B which are shown with vents 97C formed therein and which puncture a frangible top 105 of the cup cartridge. The cutting elements are optional because the user may remove the frangible cover and in such cases a cover 92 does not need to have cutting elements 97B. The cup cartridge 98 is of a size and shape to fit within the heater chamber 96 and is shown containing organic material 500. In some instance the cartridge 98 may have one or more of a heat transfer body 104 to facilitate heat transfer and a frangible cover 105 to seal a prefilled cartridge.

FIG. 11 shows an inserted frangible cartridge and FIG. 12 shows the inserted cartridge. The method of use includes puncturing the cartridge into at least the cutting element 109A and optionally 109B. In the post puncture position after a cartridge has been inserted into the device and the cover 92 attached. The frangible cover 105 of the cartridge 98 is punctured to allow vapor to flow into the fluid pathway 93B. The cover 92 may have seals 110 to form a better closure between cover and case. In some instance the cartridge 98 will be scarred by the heating process. A scarred cartridge which may be more frangible post heat scarring discourages reuse of non-reusable cartridges. Paper, fibers such as cotton and hemp, metal, foil, plastic, resins, thermo plastics, ceramics, ceramic doped paper, glass, and combination thereof may be suitable material for some or all of the cartridge. The cartridge maybe made of different materials in different regions.

Figure 13:
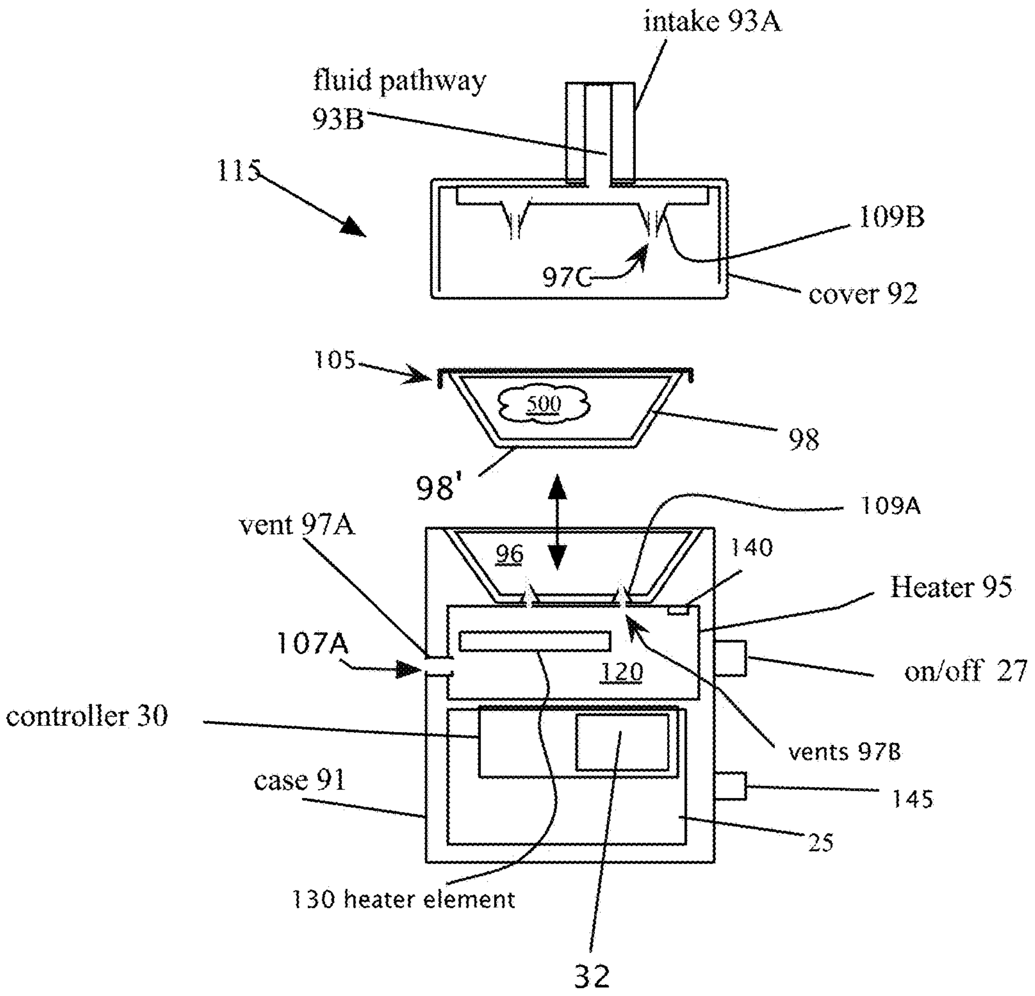
FIG. 13 illustrates aspects of a disposable drop-in cartridge module and heater.

FIG. 13 shows a convection heater in a cartridge vaporizer system 115 utilizing the basic components of the system illustrated in FIGS. 10-12 but using a convection manifold as the heating engine to supply heat the material. Main elements of the heater 95 are a manifold 120 a heating element 130 and a thermistor 140 in signal communication with the controller 30 which may include memory 32. Not shown are the electrical connections, which are known in the art. The heater heats air which has been drawn in from the outside of the case through the vent 97A. The thermistor (or other temperature sensor) 34 is used by the controller 30 to determine the temperature of the air heated in the manifold 120. A signal communication light 145 such as LED (light emitting diode) also in signal communication with the controller 30 at least one of changes color, lights up, flashes and goes steady state when the temperature in the manifold is adequate to vaporize the material 500 (or extract). The user then inhales on the intake 93A and heater air in the manifold exits the manifold through the vents 97B contacting the material 500 and forming vapor which is drawn out of the cartridge 98 through the third vents 97C. Within the is the heater chamber 96 of a predefined shape and vent 97A opening through which is formed a fluid pathway 107A from the exterior of the case 91 to the interior. Vents 97B provide a fluid pathway through the bottom cutting elements 109A into the bottom 98' of the cup cartridge and communicate from the interior of the case into the cartridge. The cover can have top cutting elements 109B which are shown with vents 97C formed therein and which puncture a frangible top 105 of the cup cartridge. The cutting elements are optional because the user may remove the frangible cover and in such cases a cover 92 does not need to have cutting elements 97B.

Figure 14A:
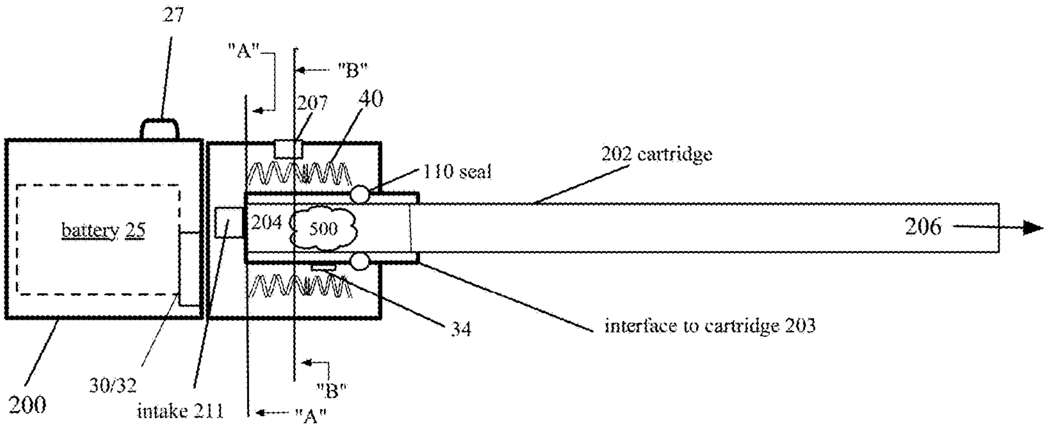
FIGS. 14A-14C illustrate aspects of a cartridge module and heater.
Figure 14B:
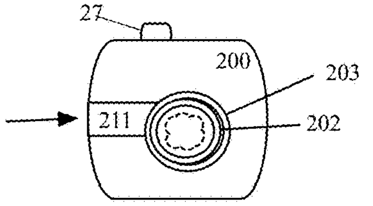
Figure 14C:
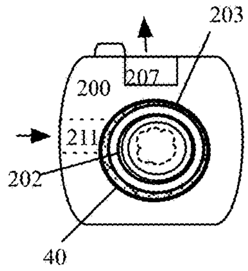

FIGS. 14A-14C show a non-pass through cartridge heating system, device and method. A case 200 and contains the one or more heating elements. Heating elements may be coil wire, filament, metalized film, metalized silicon, or any suitable resistance material for electrical heating. The cartridge 202 is shown as roughly tubular with a distal containment end 204 containing material 500 and with a divider 15 from the proximal end, and a proximal 206 inhalation end together forming a fluid pathway. The inhalation end is a fluid pathway from the distal end. One or more heater elements 40 are placed in thermal contact with the distal end whereby the material in the cartridge can be heated to a SET. Thermal contact is when the heaters are air from a manifold are in close enough proximity to the material 500 sought to be vaporized to transfer temperature to that material at the desired level to achieve the vaporization. One or more vents 207 allow the heater to vent from the case. At least one air intake 211 provides a fluid pathway for air to enter the case and be drawn through the cartridge from distal end to proximal end and then out for inhalation. An on/off switch 27 turns on the system. The controller 30 receives input from one or more of temperature sensor 34 and controls the power from the battery to the heater to maintain SET for vaporization. FIG. 14B shows a cut away view of the device along the line of “A-A” and FIG. 14C shows a cut-away of the device along the lines of “B-B”.

Figure 14D:
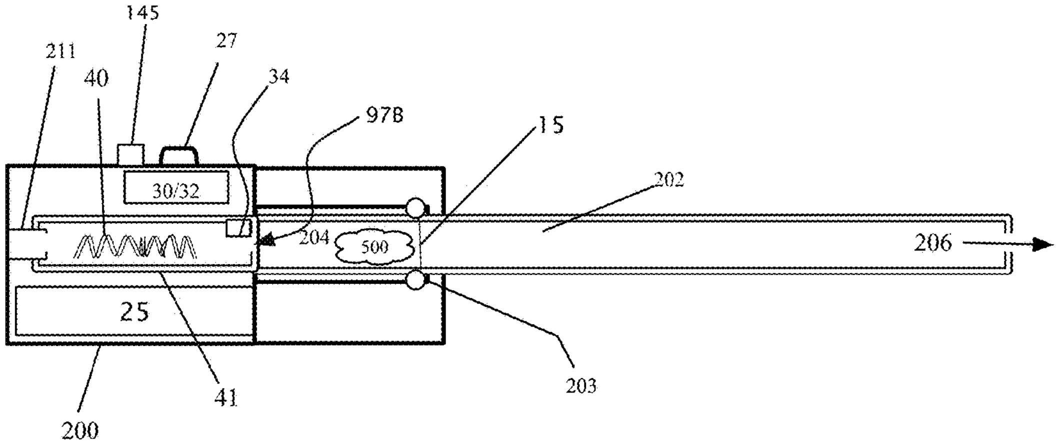
FIG. 14D illustrate aspects of a heater with manifold and a disposable cartridge.

FIG. 14D shows a non-pass through cartridge heating system, device and method. The case 200 contains the convection heater manifold 41 forming a fluid pathway from the air intake 211 to the distal end 204 of the cartridge. The cartridge fits into an interface 203 in the case whereby the distal end 204 of the cartridge (the air intake end “AIE”) which contains material 500 to be vaporized is placed in proximity to the heater manifold 41. A divider 15 is formed between the distal end and proximal end. An organic material 500 for vaporization is within the distal end near the manifold 41 outlet vents 97B. The proximal end 206 is an inhalation end (“IE”) and is extended from the case. The manifold contains one or more heating elements 40. Heating elements may be coil wire, filament, metalized film, metalized silicon, or any suitable resistance material for electrical heating. The cartridge 202 is removable from the case. The cartridge fits into interface 203 whereby the distal end 204 of the cartridge is within the case and the proximal end 206 is extended from the case. The controller 30 receives input from one or more of temperature sensor 34 and controls the power from the battery to the heater to maintain SET of air in the manifold for optimal vaporization. Organic material 500 for vaporization is within the distal to receive heated air from the manifold. In use, an air intake 211 provides a fluid pathway for air to enter the manifold 41 and is then drawn through the vents 97B out of the manifold into the distal end to proximal end and then out for inhalation. A user presses the on/off switch which may activate a signal communication light 145 such as LED in signal communication with the controller 30 which will at least one of changes color, lights up, flashes and goes steady state when the temperature in the manifold is adequate to vaporize the material 500 (or extract).

Figures 15A, 15B, 15C:
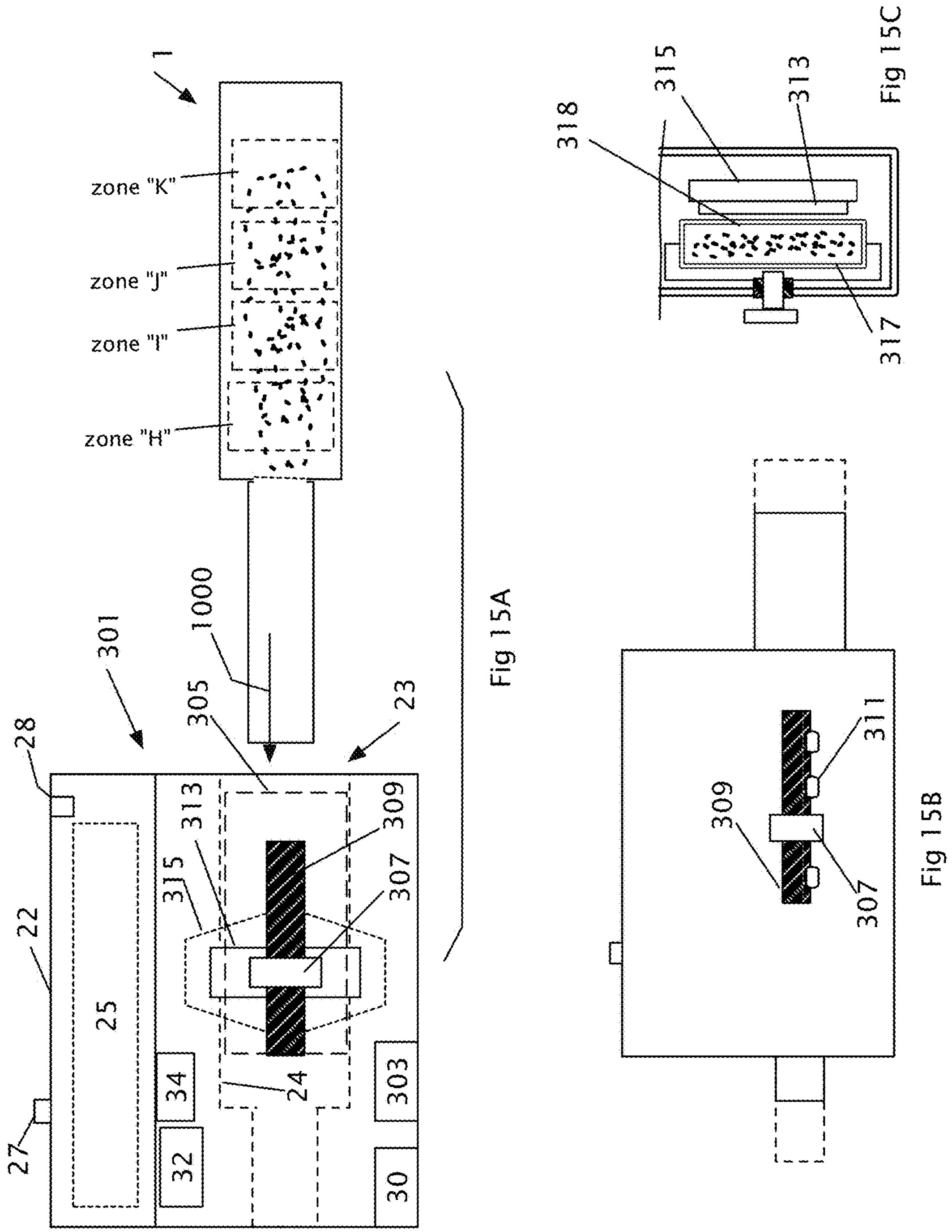
FIGS. 15A-15C illustrate a linear moving zone heating system and method.
Figure 15G:
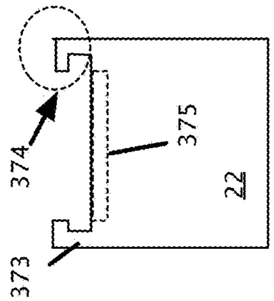
FIGS. 15E-15G show a side, top and back view of the base of the vaporizer. Shown in FIG. 15D.
Figure 15D:
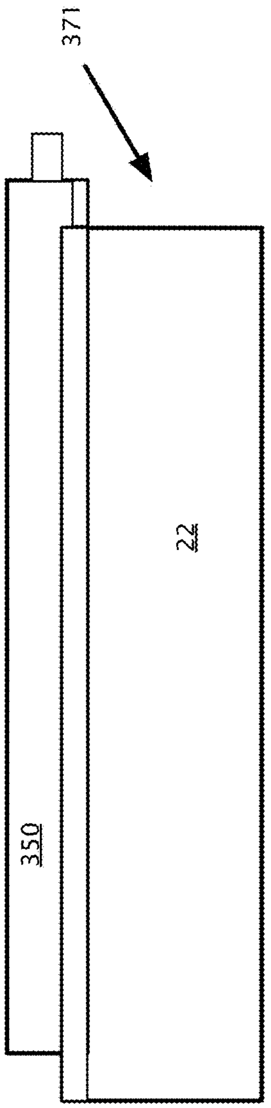
FIG. 15D shows a side view of a vaporizer system with sliding cartridge.
Figure 15E:
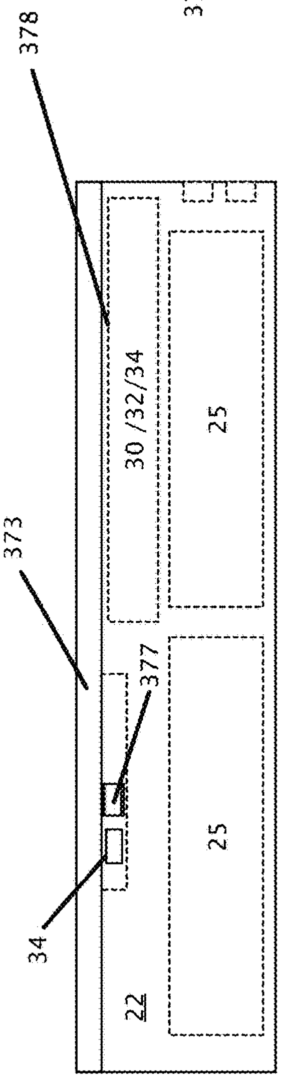
Figure 15F:
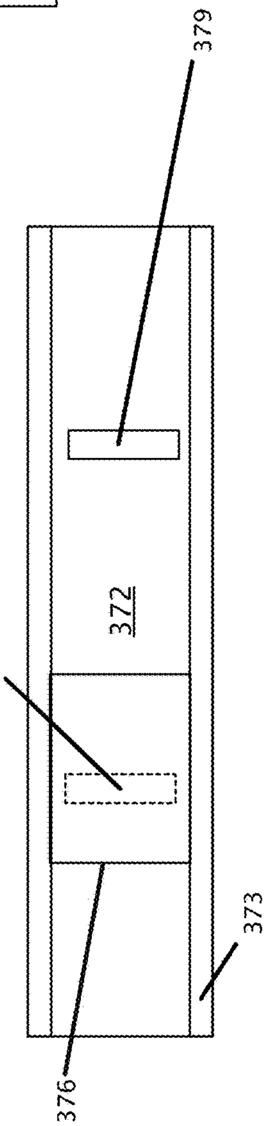

FIGS. 15A-16M show a heater system and device 340 wherein a heater encasement has a receiver 23 which allows insertion of a cartridge 1. FIGS. 15A-15C show aspect of a sled moving system with a single heater. The cartridge shown outlines 4 cartridge zones “H-K” for heating, the zones correspond to the approximate size of the area heat is being applied to from the device. A battery 25 supplies power on demand. Controller 30, memory 32 and temperature sensor 34 are also shown. The heater system 301 which has a single region which is the outlet for heat and it is of a size that corresponds roughly to the size of one cartridge zone which is fixed. One or more vents 303 may be provided. The flat cartridge shown may be advantageous in that it has a greater surface area facing the heating element than a cylindrical cartridge and will heat the material or extract therein in accordance with the heat transfer over the flat area. In this instance a sled 305 within the case reversibly mates with a cartridge 1. The sled 305 is connected to a lever 307 which extend outside of the case and moves within a fixed track 309. A series of tabs 311 may be formed in the track to provide tactile feedback to a user, through the lever, as the lever passes along the track and encounters a tab. The tabs approximate cartridge position in the device. The lever 307 is used to move a cartridge mated with a sled forward or back in a line within the case. The movement is used to align different portions of the cartridge with the single zone heating element 313 and insulation layer 315 is between the heating element and case. The back wall 317 of the cartridge is shaped to fit in the sled 305. That wall may be textured, or have magnetic or metal portions thereon to facilitate a good fit. The front wall 318 of the cartridge may be a dissimilar material than other portions of the cartridge. The front wall may be mesh or vented or textured. The front wall may be constructed of a material or with surface features to at least one of promote, reduce or control heat transfer.

In this exemplary, or any of the cartridge exemplary at least a portion of the cartridge may have a temperature sensitive dye or material therein which changes color once the cartridge has been used to alert the user (or a sensor) that it is a used cartridge. The cartridge mates with the cartridge guide which places it adjacent to heating elements.

It should be constructed so that it does not burn, or combust at the selected exposure temperatures (SET). SET is selected from the group consisting of about 380 degrees F., 390 degrees F., 400 degrees F., 410 degrees F., 420 degrees F., 430 degrees F., and 440 degrees F. In some instance the failure to burn or combust at the SET is for a one minute exposure. In some instances that failure to burn or combust at the SET is for at least a two minutes exposure. In some instances that failure to burn or combust at the SET is for at least a three minutes exposure.

It is preferred that he failure to burn or combust at the SET is for after at least two, one minute exposures. It is more preferred that the failure to burn or combust at the SET is for at least three, one minute exposures. It is still more preferred that the failure to burn or combust at the SET is for at least five, one minute exposures. It is yet more preferred that the failure to burn or combust at the SET is for at least six, one minute exposures. It is most preferred that the failure to burn or combust at the SET is for at least eight, one minute exposure.

FIGS. 15D-15M show a system and components supporting a method of heating another linearly moving reusable cartridge. Although the cartridge is shown as refillable, those of ordinary skill in the art will recognize that a disposable cartridge is within the scope of the disclosure and replacing the reusable cartridge with a disposable cartridge or nesting a secondary disposable container in the area of the heating chamber for the reusable cartridge is within the scope of this disclosure.

The device 371 includes a base 22 having a receptacle 372 to receive a carriage 350 with a material chamber. The base also may include carriage guides 373 to position an insertable cartridge. A catch 374 may also be provided. Catch(es) may be combined with a guide to position a sliding cartridge and to limit its removal to certain orientations. A heater region 375 is provided in the receptacle. The heater region 375 is surrounded by one or more of a buffering region 376 of ceramic, steel, glass, aluminum, composite or the like to both allow for a conduction heating element 377 to provide heat through a heater region 375 which is a plate or tile that heats up and via primarily conduction to heat transfer to plant material, extract or a cartridge in close proximity to it's surface. Heaters may be conductive plates with filament, coil or metalized resistance heaters thereon or ceramic tiles with resistance wires therein. A contact strip 379 may be added to connect with contacts to activate positioning lights or vibration or other alarm. Indicator light 325 which may be colored LEDs or the like (such as green and red) can be lit by the controller to indicate status of positioning. Two lights shown is not a limitation and more than two may be used. Red may mean out of power. Green may mean go. Yellow may mean spent cartridge. The communication may be of a spent cartridge, a spent zone that has been heated, the remaining zones to heat, a need for recharge, or remaining zones to heat.

The heating element 377 in preferred to have a total resistance of about 1 to about 8 Ohms, and more preferred to have a total resistance of about 2 to about 6 Ohms and most and more preferred to have a total resistance of about 3 to about 5 Ohms. Of course the selection and size of heater region material and buffer region material may change the preferred Ohms. Materials with higher thermal conductivity W/m·° K (BTU·in/ft$^2$·hr·° F.) may require less energy to heat the heater region to the predetermined temperature.

A circuit board which connect the battery power supply to the heating element 377 also contains a microprocessor controller 30 which has memory 32 and which controls certain operations of the vaporizer device. One or more temperature sensors 34 may also be included. Operations controlled may include one or more of time, date, location, security code, on/off, sequence of heating, temperature, indicator display of the heater, battery charging, battery management, gps, wireless communications, wifi or bluetooth communications, battery state of charge indication, cartridge verification, wireless or wired input/output. Those of ordinary skill in the art will recognize that bluetooth or other wireless or wired connection to a smart phone or computer may also be used to perform some of the controller functions and that would be within the scope of this disclosure. The battery supply 25 is used to power the device. The controller 30 controls the flow of power to the heating element and may use pulse-width modulation (PWM) or other schema to maintain the temperature of the heating element at a predefined temperature. A PCB board is within the base and contain microprocessors, memory, controllers, is connected to sensors, connections to on/off switches, connections to I/O, connection to battery supply and the like. Not shown are the electrical connections between the electrically powered components and between the controller and electrical components which are well known in the art.

Figures 15H, 15I, 15J, 15K:
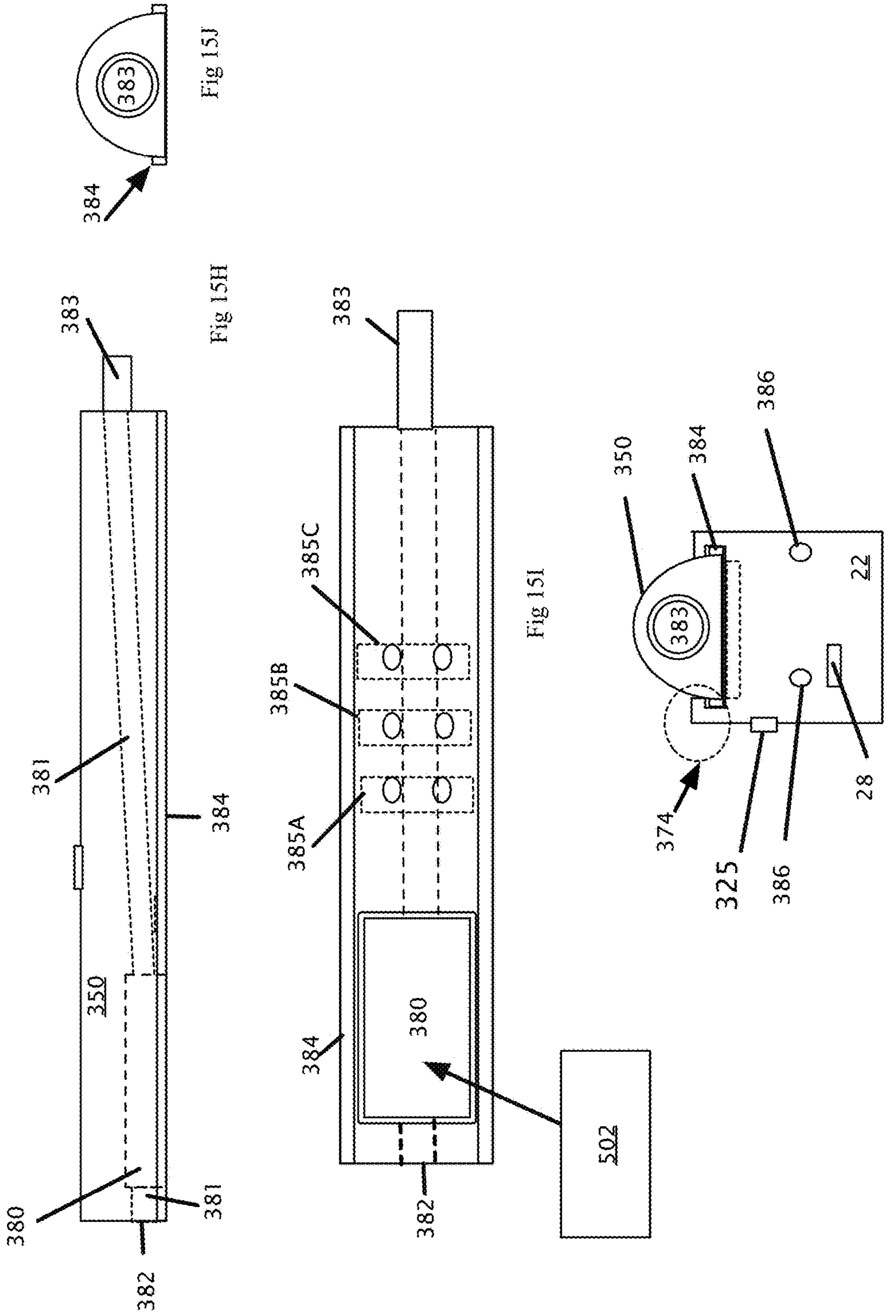
FIGS. 15H-15J show a side, bottom and back view of the sliding cartridge of FIG. 15D.
FIG. 15K shows a back view of a sliding cartridge of FIG. 15D.

FIGS. 15H-15J show aspects of the cartridge 350. This carriage has a chamber 380 which is in the midst of a fluid pathway 381 which passes through the chamber 380. The chamber is open on one side with fluid connections (not shown) and is constructed of a material which can withstand heating by the heater region 375. The fluid pathway has an intake opening 382 a long pathway 381 which passes through the fluid connection in the chamber and an inhalation opening 383. The carriage catches 384 mate with carriage catches 374 to limit the carriages movement in the receptacle. A series of pairs of contacts (385A-385C) may be added which are activated via the contact strip 379. By positioning a contact pair in electrical contact with a contact strip a light, or other visual or auditory indicator of a predetermined position may be activated. The contacts help a user positioning the chamber 380 at predetermined intervals along the chamber 380. In some instance a disposable cartridge 502 containing material or extract or both is fitted into the chamber 350 and disposed of after use.

For a non-electrical feedback mechanism on position, the contact strip may be replaced by a bump or divot and the contacts may be replaced by pups or divots which that a tactile response can be generated when a pair of contacts pas over a contact strip.

Figure 15L:
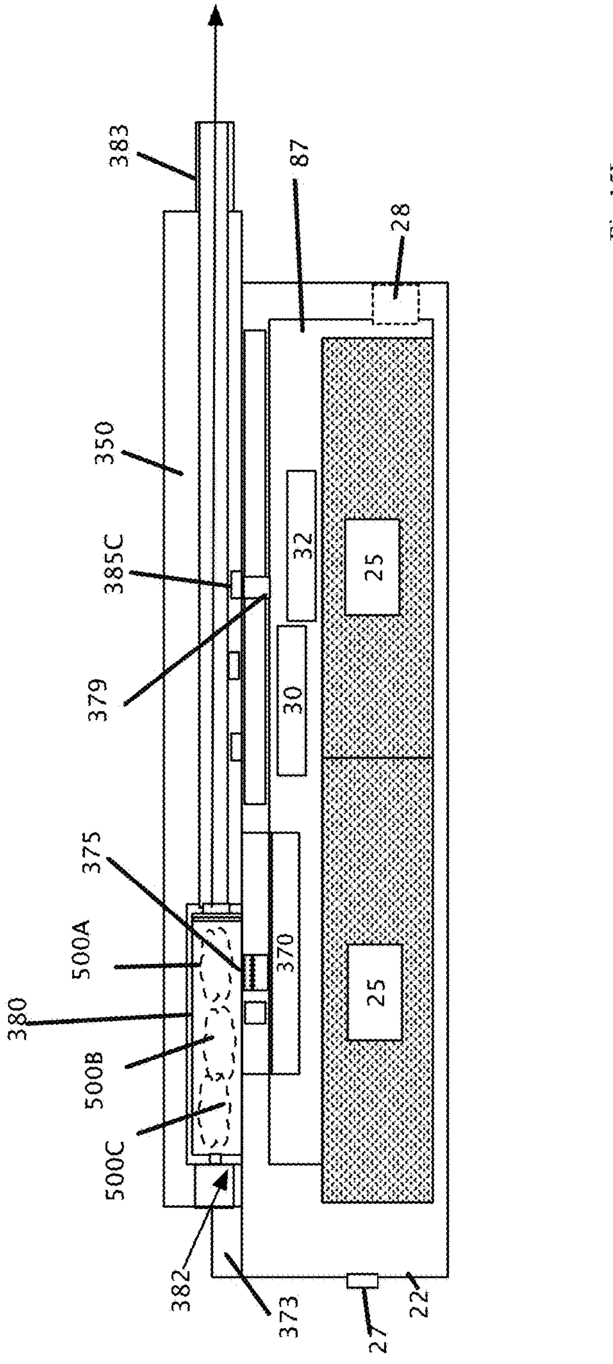
FIGS. 15L-15M illustrate sequenced zone heating of the cartridge in FIG. 15D.
Figure 15M:
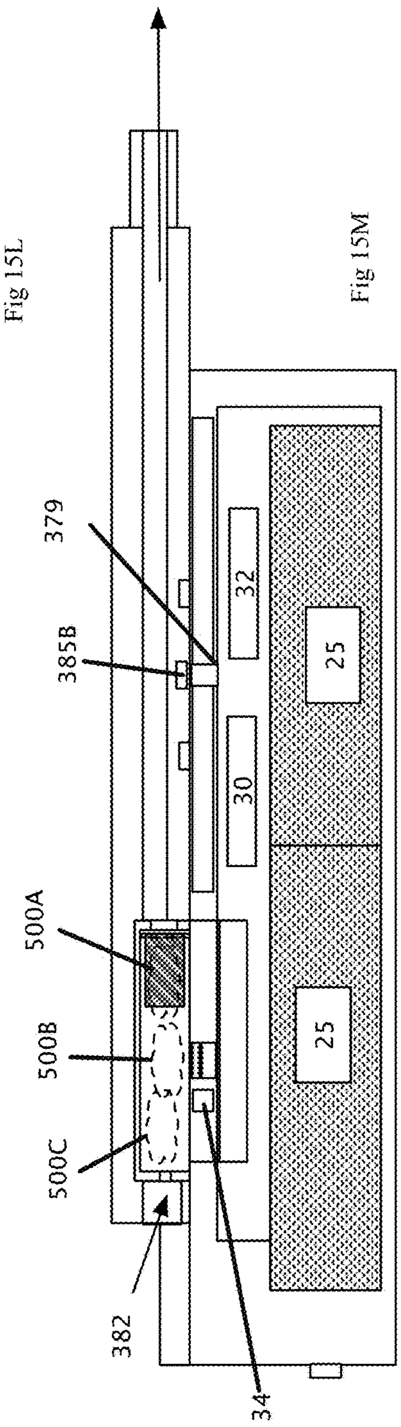

An assembled device shown in FIGS. 15K-15M has a carriage 350 mated to a base 22. A input output 28 through the base is shown and indicator lights 386 are visible. Such lights can convey state of charge, temperature, position of carriage and the like.

The chamber 380 is larger than the heating element 375 and wherein the heat from the heating element 377 transmitted through the heater region 375 has direct thermal contact with a portion of the material in the chamber. The movement of the carriage, associated chamber and material therein is done be relocating the carriage relative to the heater region 375. The movement of the chamber relative to the heater region is used to move a new region of material (in the chamber) into direct thermal contact with the heater region. Movement in this instance is along the receptacle and the figures illustrate positioning plant material portions 500A-500C, which a user places in the chamber, over the heater element 375. Those of ordinary skill in the art will recognize that the movement of portions of the material in the chamber may be accomplished by rotating a circular chamber wherein a heater region is a pie shaped swede that only heats a portion of the material in the circular chamber is within the scope of this disclosure as it is moving material in a chamber sub portion at a time into direct thermal contact a portion at a time and such a rotational movement is also within the scope of this disclosure.

The sequence of use is such that a user slides the carriage to a position whereby material 500A is positioned over the heater element 375. As the heater element heats and vaporizes organic material from the material the user inhales on the inhalation opening thereby causing air to move through the fluid pathway 381 and draw with it the vapor. After a portion of material 500A has been heated the user moves the carriage forward and material portion 500B is placed over the heater element and the sequence repeats until the material has been utilized.

Memory can keep track of the movement of the carriage (which contacts have been closed) and prevent heating of a region previously heated. To reduce heating (with hot vapor) unused material the air pathway passes over the unheated portion(s) of material 500B and 500C then over the heated portion 500A, otherwise hot vapors will heat the material in the portions which are placed remote from the heater element.

The contact strip 379 is shown during the sequence of use in FIGS. 15L and 15M first contacting contact pair 385C provides indication that the chamber is positioned properly, then pair 385B provides indication that the linear movement of the chamber forward is successful to place material in the right proximity to the heater.

FIGS. 16 and 17 shows a two part cartridge 400. The cover is a generally tubular form with an annular wall 402 and open ends 403. A fluid passage 404 is formed inside. Preferable the cover is generally trapezoidal, rectangular or ovoid whereby it has a floor "F" which is longer than the side region "S". A carrier 406 is of a size and shape to slide into and nest tightly into the cover 401. The carrier is an open structure with sidewalls 407, a floor 408 which is shown divided into a first sections 410A and a second section 410B and one or more dividers 412. Dividers may be added to reduce the opportunity for plant material or concentrate to become disengaged from the carrier. The dividers are permeable to air flow. The first section 410A is an inhalation fluid pathway with an inhalation end "IE". The second section 410B is a material containment chamber to hold and expose plant material or extract to heat with an air intake end "AIE". They may be mesh, slotted, perforated or have vents whereby air inhaled can pass through the cartridge 400.

The cartridge portion for containment will be heated to vaporize. It should be constructed so that it does not burn, or combust at the selected exposure temperatures (SET). SET is selected from the group consisting of about 380 degrees F., 390 degrees F., 400 degrees F., 410 degrees F., 420 degrees F., 430 degrees F., and 440 degrees F. In some instance the failure to burn or combust at the SET is for a one minute exposure. In some instances that failure to burn or combust at the SET is for at least a two minutes exposure. In some instances that failure to burn or combust at the SET is for at least a three minutes exposure.

It is preferred that he failure to burn or combust at the SET is for after at least two, one minute exposures. It is more preferred that the failure to burn or combust at the SET is for at least three, one minute exposures. It is still more preferred that the failure to burn or combust at the SET is for at least five, one minute exposures. It is yet more preferred that the failure to burn or combust at the SET is for at least six, one minute exposures. It is most preferred that the failure to burn or combust at the SET is for at least eight, one minute exposure.

FIG. 18 shows an example of an optional marked version of the exterior of the cartridge. The markings 416 are visual cues. They may also be indentations and be tactile cues and are used for positioning and moving a cartridge in a heater. FIG. 19A is a cutaway view of FIG. 18 along the line of "A-A". FIG. 19B is a cut-away view of FIG. 18 along the line of "B-B".

FIG. 20 is an alternate configuration which adds an alignment key 420 to help align top and bottom areas of a cartridge. The top area has one less wall between it and the heaters. In some instance a cartridge may be aligned with the double walled bottom nearest the heater zone or ones. In other instance the single walled top of the cartridge may be closest to the heater zone or zones. The alignment key mates with a receiver wherein the cartridge is positioned in a predetermined orientation.

FIGS. 21A-21C show alternate cartridge covering exemplars. A partial cover 425 is shown which fits over the open top of the carrier 426. A insert cover 427 is shown which fits inside the interior side walls of the carrier. Foil, laminate, paper, fabric, plastic and Mylar are suitable materials. The cover may also extend beyond the edges of the carrier 426 as a flexible cover 428 is shown sealed to the top of the carrier. Sealing may be via heat weld or adhesives.

FIGS. 22A-22B show aspects of a tubular two part cartridge 430. At least part of which is disposable. The first section 410A has an asymmetrical wall 432 which and open top 433 an interior annular wall 434 a larger internal diameter receiver end 435 and a vapor/air permeable divider 412 to prohibit material from easily passing into the interior above the divider. A second section 410B is also tubular. It has an air intake end 436 and a receiver mating end 437 which fits snugly into the receiver 435. Material (or extract) 500 is placed into the interior 438 of the second section. A divider 412 keeps the material from easily falling out of the cartridge. The sections may be made of dissimilar materials. The second section 410B may be designed for thermal transfer and to withstand an exterior temperature of up to 420 degrees F. for a preselected period of time. The first section 410A may be constructed to have greater insulation or tactility than the first section. The first section may be constructed of lower melting or burning point materials such as plastics. The second section may be constricted of paper, wool, blends, fabric, hemp, ceramic, metal, high temperature plastic and/or combinations thereof.

Optionally a cover 439 is fitted over the air intake end. A second or alternate cover (not shown) may also be fit over the open top. For pre-packaged cartridges snug covers can be used to one or more of limit or reduce oxidation, prevent smell, provide security and otherwise preserve the material. The cover may be pressure fit, screw fit, glued, sonic welded. The cover may be frangible.

FIGS. 23A-23G show a heater base for use with disposable (or refillable) cartridges and the use of that system. The heater base has the advantage of keeping very clean. The cartridge mates with the base but all flow of vapor s within the heated cartridge thereby keeping the heater clean and without vapor residue. When a cartridge is used it is disposed of.

The heater 440 has a case 442 with a cartridge interface 444 therethrough. Optional key guides 445 for a cartridge with alignment keys 420 are illustrated but they are optional. An on/off switch 446 is shown and an illuminated indicator 447. A battery 25 is inside the case, as is a controller 30, optional I/O optional memory 32, and optional wireless connection via wifi or Bluetooth or the like 33. A recharge connection 448 communicates through the case for recharging the battery. A cartridge sensor 449 may be added within a cartridge interface 444. a thermistor 140 in signal communication with the controller 30 The sensor interrupts power to the one or more heater elements 40 if a cartridge is not present in the interface.

FIGS. 23C and 23D show a heater 440 with a cartridge 400. The cartridge fits into the interface 450. The front side

Figure 23G:
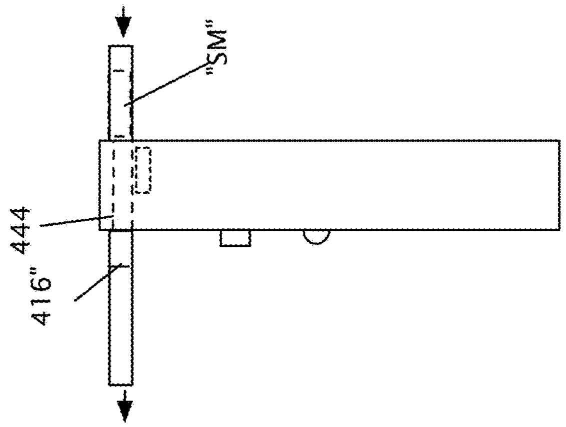
Figure 23F:
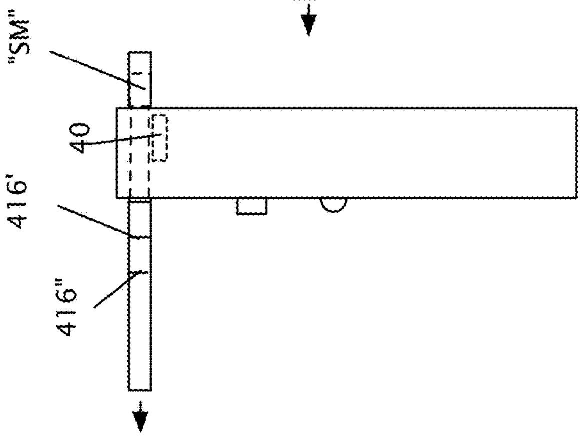
Figure 23E:
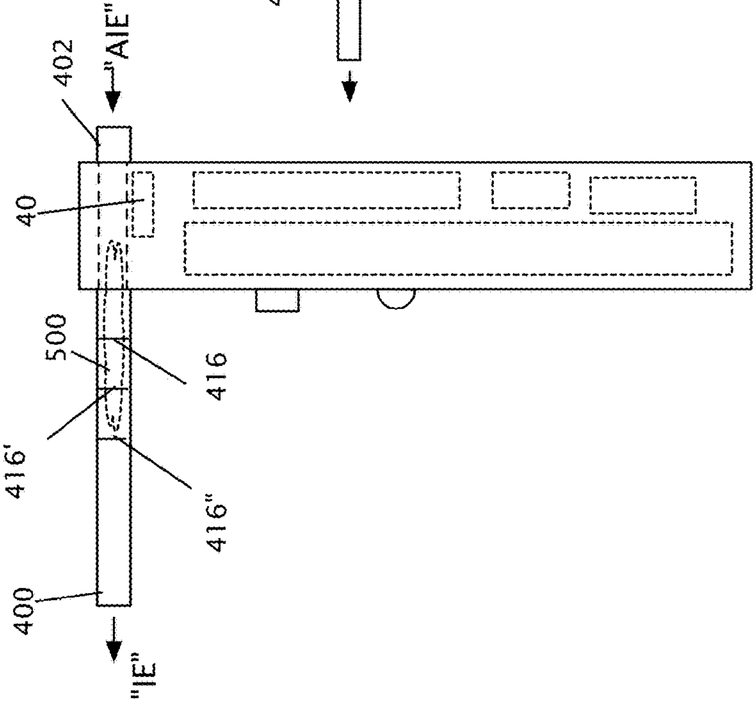

442' of the heater unit is shown with a cartridge 400 inserted thereform in to the interface 450. During use the cartridge can be moved, via pushing it from the front side 442' of the heater towards the backside 442". FIGS. 23E-23G show the use of a cartridge in the heater unit in a sequence of use. The inhalation end "IE" is where a user inhales and airflow enters the cartridge through the air intake end "AIE". Optional visual cues 416-416" on the cartridge cover can be used to approximate the movement of cartridge portions over heater 40 element(s). Positional tabs 417 may also be provided whereby an inserted cartridge activates a sensor or actuator to identify the presence of a cartridge and/or the position of the cartridge or movement of the cartridge in a receiver. As the cartridge is pushed through the area of spent material "SM" within the cartridge increases in amount until the cartridge is finished and then disposed of. In some instance a user may reuse a cartridge, if it is constricted of material suitable for multiple uses.

FIGS. 24 and 25 show additional exemplars of a smartphone or other power supply connectable heater and cartridge interface 444. The smart heater head 452 has a I/O plug 453 for a I/O on a smart phone or other power supply, it also has at least a controller 30 and an on/off switch 446. A slave heater 454 is shown in FIG. 25 which has no controller—but rather through the I/O leverages the control processing power of a smart phone or other device with a microprocessor and/or controller.

FIG. 26 is a flow diagram of aspects of a method of operation of a zone cartridge heating system utilizing a heater and cartridge. Not all steps are required a subset with fewer decisions are within the scope of this disclosure. First a controller using one or more of decision engines and rule engines, decides if a cartridge is present in a receiver 460. A sensor including but not limited to actuators which may be optical, magnetic, mechanical or electrical is switched on if a cartridge is present. If no cartridge in receiver then the controller decides do not heat 461. The controller then determines if a previous cartridge had been removed 462 which would indicate a new cartridge is present. Optionally the controller may review its memory to determine if the cartridge in the receiver is used 463. If a used cartridge the controller may decide do not heat 461. Signs of used would include, but are not limited to, a frangible tabs broken, a heat effected region on the cartridge identified by an optical sensor as being previously heated, a unique identifier code optically scanned and determined by memory to have been previously used. If the cartridge is determined to be new the controller will start or initiate the sequence of heating 465. If a cartridge was previously in the receiver the controller will determine if the entire heating cycle of the last zone heated was competed 466. If a new cartridge is being heated the controller will determine when the heating of the current zone is completed 466. If the cycle time to heat a zone is not competed the controller will allow the device to continue to heat the zone 467. If the cycle time to heat a zone is competed the controller will determine if additional zones are available to heat 468. If yes, then the controller will continue to power the heating of the next remaining zone 469.

A multi zone heater will have two or more heating elements forming zones, a cartridge will be inserted and will remain in place during heating. The zones are selected by the controller turning on or off power to different heating elements.

For a single heating element used to heat multiple zones of material in a cartridge the user moves the cartridge. For a moving cartridge additional controller steps are illustrated. The controller will alert the user to move the cartridge 470. That alert is via a visual, auditory or other communication such as a LCD screen icon, a LED blinking or changing color or a sound. The controller will then determine if the user moved the cartridge to a next zone 471. Determination of movement of the cartridge is generally the same type of sensor or actuator used to determine if the cartridge has been inserted.

The controller accesses a look up table (LUT), set by the user or set by the software to keep the temperature of one of the manifold and the area near the cartridge at the SET. The controller clock also measures the time the heating element is at SET or the time the cartridge or a selected portion thereof is exposed to temperature at SET. The time may be fixed or variable.

It will be understood that various aspects or details of the disclosures may be changed combined, or removed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

What is claimed is:

1. The vaporizer system with a disposable cartridge comprising:

a case (91) having a heating chamber (96) to receive a disposable cartridge comprising;

an open top which mates with a cover (92);

a heater manifold (120) with an inlet vent (97A) and an outlet vent (97B);

a first cutting element (109A) in the bottom of the heating chamber with the outlet vent passing there through;

a heating element (130) within the manifold;

air intake vents (97A) into the manifold;

heated air vents (97B) for air exiting the manifold to enter the cartridge;

an on/off switch;

a battery;

a temperature sensor (140) in proximity to the outlet;

a controller in signal communication with the heater element, battery, temperature sensor and the on/off switch;

a cover having an intake (93A) with a fluid pathway (93B) therethrough which mates with the open top;

a disposable cup cartridge (98);

whereby pressing the cup cartridge into the heating chamber causes the first cutting element to pierce the bottom of the cup cartridge (98'); and, whereby pressing the on/off switch turns on power to the heater.

2. The vaporizer system with a disposable cartridge of claim 1 further comprising: a frangible cover (105) over the cup cartridge; a second cutting element associated with the fluid pathway; and, whereby the second cutting element pierce the frangible top when cover is mated to the case forming a fluid pathway for vapor.

3. The vaporizer system of claim 1 wherein the controller keeps the heat in the manifold generally at the SET for a fixed time.

4. The vaporizer system of claim 3 wherein the controller stops the heating when the fixed time has been reached.

* * * * *